(12) United States Patent
Trepanier et al.

(10) Patent No.: US 12,289,489 B2
(45) Date of Patent: Apr. 29, 2025

(54) PATIENT SUPPORT APPARATUS SYSTEMS WITH TELEVISION DETECTION

(71) Applicant: Stryker Corporation, Kalamazoo, MI (US)

(72) Inventors: Jerald A. Trepanier, Augusta, MI (US); Jonathan A. Hietbrink, Plainwell, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/572,643

(22) PCT Filed: Jun. 28, 2022

(86) PCT No.: PCT/US2022/035358
§ 371 (c)(1),
(2) Date: Dec. 20, 2023

(87) PCT Pub. No.: WO2023/043519
PCT Pub. Date: Mar. 23, 2023

(65) Prior Publication Data
US 2024/0283996 A1    Aug. 22, 2024

Related U.S. Application Data

(60) Provisional application No. 63/244,768, filed on Sep. 16, 2021.

(51) Int. Cl.
*H04N 21/422* (2011.01)
*A47B 97/00* (2006.01)
(Continued)

(52) U.S. Cl.
CPC ....... *H04N 21/4222* (2013.01); *A47B 97/001* (2013.01); *H04N 21/42684* (2013.01); *H04N 21/436* (2013.01)

(58) Field of Classification Search
CPC ......... H04N 21/4222; H04N 21/42684; H04N 21/436; A47B 97/001; G16H 40/60; G08B 29/00; G08B 21/182; H04L 67/12
(Continued)

(56) References Cited

U.S. PATENT DOCUMENTS 10,235,845 B2   3/2019  Bhimavarapu et al.
10,257,063 B2   4/2019  Bhimavarapu et al.
(Continued)

OTHER PUBLICATIONS

International Search Report and Written Opinion, PCT/US22/35354, dated Sep. 26, 2022, 17 pages.

*Primary Examiner* — John W Miller
*Assistant Examiner* — Omer Khalid
(74) *Attorney, Agent, or Firm* — Warner Norcross + Judd LLP

(57) ABSTRACT

A headwall unit is mounted a headwall of a hospital room and acts as a communication conduit between a bed (or other patient support apparatus) and a conventional communications outlet built into the headwall of the hospital room. The communications outlet is communicatively coupled to a standard nurse call system and an in-room television. The headwall unit is adapted to wirelessly forward audio signals from a remotely positioned nurse to the bed, and to receive wireless audio signals corresponding to a patient's voice from the bed and to forward the received audio signals to the communications outlet. The headwall unit is further adapted to detect infrared communications from both the bed and a television remote control. Communications from the television remote control are automatically analyzed by the headwall unit to determine the type of television in the room and the correct signals to use for controlling the television.

18 Claims, 14 Drawing Sheets

(51) Int. Cl.
*H04N 21/426* (2011.01)
*H04N 21/436* (2011.01)

(58) Field of Classification Search
USPC .................................... 348/734; 340/286.07
See application file for complete search history.

(56) References Cited

U.S. PATENT DOCUMENTS

| | | |
|---|---|---|
| 2014/0247399 A1* | 9/2014 | Butler ................ H04N 21/2143 |
| | | 348/734 |
| 2019/0046379 A1 | 2/2019 | Constant et al. |
| 2019/0150737 A1 | 5/2019 | Bodurka et al. |
| 2019/0183705 A1* | 6/2019 | Bodurka .................. H04B 5/72 |
| 2019/0188992 A1 | 6/2019 | Bodurka et al. |
| 2020/0327784 A1 | 10/2020 | Bodurka et al. |
| 2022/0301416 A1 | 9/2022 | Bodurka et al. |
| 2023/0110653 A1 | 4/2023 | Bodurka et al. |

\* cited by examiner

A-Mark 0003
A.R. Systems 0037 0556 0374 0455
Abex 0032
Accent 0009 0037 0556
Accuphase 0556 1909
Acec 0012
Adcom 0625 0284
Admiral 0093 0363 0418 0087 0305 0163 0264
Adventura 0046
Adyson 0068 0217 0216 0032
AEA 0037 0556
Agashi 0216 0264 0217
AGB 0516
Agef 0087
Aiko 0092 0009 0037 0556 0216 0371 0035 0433 0072 0361 0191 0264 0217
Aim 0037 0072 0412 0556 0753 0208 0706 0805 0068
Aiwa 0705 0701 1904 1916 1908 1914 1915
Akai 0030 0361 0208 0371 1537 0037 0803 0433 0745 0191 0702 0035 0284 0672 0009 0696 0072 0753 0218 0806 0729 0714 0163 0516 0715 0602 0556 0548 0581 0480 0217 0631 0216 0264 0448 0178 0329 0377 0606 0708 1037 1908 0473 0648
Akiba 0218 0282 0455 0037 0556 0294
Akira 0190
Akito 0272 0037 0556
Akura 0037 0556 0668 1668 0359 0412 0493 0009 0218 0282 0264 0171 0714
Alaron 0179 0216
Alba 0009 0418 0370 0235 0371 0668 0037 0556 1037 0355 0218 0216 0247 0431 0163 0487 0581 0036 1668 0579 1904 1908 0714 0443
Alkos 0035
Allegro 0720 0774
Allorgan 0206 0294 0217
Allstar 0037 0556
Ambassador 0177
Amplivision 0217 0400 0370 0320

Amstrad 0177 0009 0516 0264 0354 0371 0218 0171 0037 0556 0433 0412 0362 1037 0648 0581 1904
Anam 0037 0556 0009 0068 0180 0003 0250
Anam National 0037 0250 0556 0650
Anex 0421
Anglo 0009 0264
Anitech 0009 0068 0264 0037 0556 0282 0102
Ansonic 0370 0037 0556 0009 0668 0374 0163 0292 0102 0411 0259 0247 1437 0012 0284 0428 1904 0104 1668
AOC 0019 0030 0052 0185 0003
Apex Digital 1943
Apollo 0473
Arc en Ciel 0399 0501 0109 0196 0198
Arcam 0216 0399 0217
Ardem 0486 0714 0037 0633 0556
Aristona 0556 0037 0012
Arthur Martin 0163 0400
ASA 0105 0346 0070 0104 0087
Asberg 0037 0556 0102
Asora 0009
Astra 0037 0556
Asuka 0218 0217 0216 0264 0282 1904
ATD 0698
Atlantic 0037 0556 0216 0206 0320 0259
Atori 0009
Auchan 0163 0400
Audiosonic 0009 0037 0374 0556 0109 0714 0715 0217 0370 0337 0264 0218 0486 0428
Audioton 0217 0486 0370 0264 0428
Audiovox 0092 0451 0180 0003
Aumark 0060
Autovox 0087 0206 0544 0349 0217 0247
AVP 1904 1908
AWA 0011 0036 0009 0157 0374 0451 0412 0037 0556 0216 0606 0217 0108 0264 0785
Axxent 0009
Axxon 0714

Baird 0109 0193 0343 0190 0192 0072 0073 0217 0208 1904
Bang & Olufsen 0565 0087 0275
Barco 0380 0163
Basic Line 0374 0037 0163 0668 0556 0009 0218 0567 0282 0217 0455 0339 1037 1668
Bastide 0217
Bauer 0805
Baur 0009 0146 0303 0535 0195 0512 0037 0556 0554 0191 0361 0544 0349 1505 1010
Baysonic 0180
Bazin 0217
Beaumark 0178
Beko 0486 0035 0428 0714 0370 0418 0037 1037 0556 0606 0715
Belcor 0019
Bell & Howell 0016 0017 0154
Bennett 0556 0037
BenQ 1756
Beon 0037 0556 0418 0032
Berthen 0668 1668
Best 0337 0370 0421
Bestar 0037 0556 0370 0374
Bestar-Daewoo 0374
Binatone 0217
Black Diamond 1037 0556
Black Panther 0102
Black Star 0247
Black Strip 0035
Blacktron 0282
Blackway 0282 0218
Blaupunkt 0554 0191 0535 0195 0200 0327 0328 0448 0455 0170 0036
Blue Sky 0037 0714 1037 0487 0668 0715 1909 0556 0218 0282 0455 1934 1904 1908 1668
Blue Star 0282
Bondstec 0247
Boots 0272 0217 0009
Bosch 0320 0327
BPL 0037 0556 0282
Bradford 0180
Brandt 0625 0501 0109 0399 0196 0198 0287 0335 0471 0343 0560

Brandt Electronique 0287 0335 0501
Brinkmann 0037 0556 0668 0519 0418 0486 1668
Brionvega 0037 0556 0362 0087
Britannia 0216 0217
Brockwood 0019
Broksonic 0236 0463 0003 1905
Brother 0264
Bruns 0087 0428
BSR 0163 0294 0361
BTC 0218
Bush 0668 0218 0163 0349 0009 0036 0037 0371 0235 0282 0272 0355 0363 0374 0519 0264 0361 1037 0487 0208 0217 0698 0581 0294 0284 0556 0714 1900 1904 1908 0778 1668
Candle 0030 0056 0186
Canton 0218
Capsonic 0264
Carad 0610 0037 0556 0668 1037 1668
Carena 0455 0037 0556
Carnivale 0030
Carrefour 0036 0070 0037 0556
Carver 0054 0170
Cascade 0009 0037 0556
Casio 0037 0556 0163 0349 1904
Cathay 0037 0556
CCE 0037 0556 0217 0329
Celebrity 0000
Celestial 0819 0820 0821 0767
Centrex 0780 0826
Centrum 1037
Centurion 0037 0556
Century 0087 0247 0238
CGE 0074 0418 0247 0370 0163 0399 1904
Changhong 0827
Cimline 0009 0235 0218
Cineral 0092 0451
Cinex 0648
Citizen 0092 0451 0030 0056 0060 0186 0180
City 0009
Clairtone 0185
Clarivox 0418 0037 0556 0070 0102

FIG. 6A 154 152

Clatronic 0037 0370 0371
0714 0218 0264 0556
0217 0247 0009 0102
0320 0579 0648 1904
Clayton 0385 1037
CMS 0216
CMS hightec 0217
Combitech 1908
Concerto 0056
Concorde 0009
Condor 0320 0037 0556
0370 0216 0009 0282
0102 0247 0418 0411
0163 0264
Conia 0754 0821
Conic 0032
Conrad 0037 0556
Contec 0180 0216 0009
0185 0157 0011 0036
0264 0037 0556
Continental Edison 0501
0109 0196 0198 0399
0287 0487
Cosmel 0009 0337 0037
0556
Craig 0180
Crosley 0054 0087 0247
0074 0163
Crown 0009 0180 0712
0370 0486 0037 0556
0487 0714 0606 0715
0421 0418 0359 0579
0208 0672 0053 0339
1934 1928
Crystal 0431
CS Electronics 0216 0218
0247
CTC 0247
Curtis Mathes 0047 0466
0016 0054 0060 0093
0145 0030 0154 0451
0166
CXC 0180
Cybertron 0218
D-Vision 0037 0556
Daewoo 0092 0634 0374
0019 1909 0499 0037
0556 0009 0216 0218
0661 0217 0451 1137
1902 1928 1908
Dainichi 0218 0216
Dansai 0037 0556 0264
0032 0035 0216 0009
0036 0217 0208
Dansette 0412
Dantax 0370 0486 0714
0606 0715 1908
Datsura 0208
Dawa 0009 0037 0556
Daytek 0698 0706

Daytron 0009 0019 0374
0037 0556
de Graaf 0208 0044 0227
0163 0548 0363
DEC 0795 0785
Decca 0072 0033 0516
0037 0556 0272 0217
1137 0621 1904 1908
Deitron 0037 0556 0374
0218
Denko 0264
Denon 0145
Denver 0037 0556 0606
DER 0193 0190
Desmet 0320 0037 0556
0009 0087
Diamant 0037 0556
Diamond 0264 0698 0696
0009 0804 0825 0216
0371 0860
Digatron 0037 0556
Digiline 0037 0556 0105
0668 1668
Digitor 0037 0556
Digivision 0361
DiK 0037 0556
Dixi 0009 0037 0556 0247
0217 0087
DL 0848 0872 0780 0037
Domeos 0668 1668
Domland 0394
Doric 0349
DTS 0009
Dual 0544 0349 0217
0343 0519 0037 0556
0259 0394 0399 0303
0163 0531 1904 1137
Dumont 0017 0087 0019
0104 0102 0217 0070
0072 1904
Dunai 0544 0163
Durabrand 1437
Dux 0037 0556 0012
Dwin 0720
Dynatron 0037 0556
0012
E-Elite 0218
Ecco 0773 0706
Edison-Minerva 0487
Elbe 0435 0238 0259
0362 0292 0370 0163
0037 0556 0218 0191
0284 0411 0610 0217
0516 0361 0630
Elbe-Sharp 0516
Elcit 0087 0247 0516
0102 0163
Electroband 0000 0185

Elekta 0009 0037 0556
0264 0282
ELG 0037 0556
Elin 0216 0037 0556 0105
0104 0548 0361 0448
0305 0349 0163 0009
Elite 0218 0037 0556
0320 0305
Elman 0102
Elta 0009 0068 0264 0216
0431
Emco 0247
Emerson 0177 0180 0714
0178 0087 0179 0247
0037 0185 0556 0371
0070 0154 0019 0236
0038 0463 0282 0280
0320 0158 0361 1909
0486 0370 0163 0321
1904 1906 1905
Emperor 0282
Envision 0030
Enzer 0696 0753
Epson 0833 0840
Erres 0037 0556 0012
ESC 0037 0556 0217
Estèle 0163
Etron 0001 0037 0556
0009 0163
Eurofeel 0264 0217
EuroLine 0037
Euroman 0216 0264 0037
0556 0217 0421 0370
Europa 0037 0556
Europhon 0037 0516
0102 0163 0217 0556
0247 0431 0216
Excel 0037 0556
Expert 0206 0400 0259
0163 0305
Exquisit 0037 0556 0247
Fagor 0037 0556
Family Life 0037 0556
Fenner 0374 0009
Ferguson 0073 0625
0287 0192 0190 0335
0238 0193 0109 0560
0037 0556
0035 0343 0053 0104
0108 0361 0471 1904
0548
Fidelity 0163 0512 0171
0363 0037 0556 0371
0412 0531 0193 0216
0264 0544 1904 1906
1907 1908 0361
Filsai 0217

Finlandia 0208 0346 0359
0548 0361 0163 0363
0072 0287 0343 0045
Finlux 0105 0104 0037
0556 0714 0346 0217
0072 0163 0516 0715
0070 0087 0179 0102
0411 0631 0492 0480
0629 0473 0418 0606
0621
Firstline 0037 0556 0374
0668 0714 0163 0009
0294 0321 0216 0385
0247 1909 0102 0217
0411 0544 0349 0531
0238 0072 0235 0208
0361 1037 1668
Fisher 0104 0217 0036
0208 0370 0555 0045
0087 0157 0361 0163
0303 0544 0349 0072
0154 0047 0159
Flint 0037 0556 0610
0072 0218 0455 0264
FNR 0102
Forgestone 0193
Formenti 0163 0037 0556
0486 0216 0087 0320
Formenti-Phoenix 0216
0320
Fortress 0093 0087
Fraba 0037 0556 0370
0531
Friac 0009 0037 0556
0102 0421 0370 0499
0655 0610
Frontech 0247 0264 0349
0363 0431 0448 0217
0009 0163
Fujitsu 0179 0206 0072
0102 0217 0163 0009
0683 0037 0556 0361
0259 0853
Fujitsu General 0009
0186 0217 0206 0163
Funai 0180 0668 0179
0264 0294 0303 0412
1668
Futronic 0264 0795 0860
Future 0037 0556
Futuretech 0180
Galaxi 0102 0037 0556
0361 0163
Galaxis 0370 0418 0037
0102 0556
Galeria 0009
GBC 0163 0009 0374
0218 0363
GE 0051 0343 0047 0135
0747 0021 0174 0027
0178 0282 0451 0560
0287 0109 0335 0625
Geant Casino 0163 0400

FIG. 6B

GEC 0163 0361 0349 0037 0516 0556 0072 0217
Geloso 0247 0009 0363 0163 0374
General 0590 0109 0287 0471 0186
General Electric 0343 0287
General Technic 0009
Genesis 0009 0037 0556
Genexxa 0218 0037 0556 0412 0493 0163 0009
Gericom 0865
Giant 0217
Gibralter 0017 0019 0030
Goldfunk 0668 1668
Goldhand 0216
Goldline 0337
GoldStar 0019 0037 0009 0030 0056 0370 0001 0290 0032 0002 0377 0217 0178 0247 0216 0556 0431 0163 0361 0109 0363 0606 0044 1934 1926 0714 0715
Gooding 0487
Goodmans 0634 0374 0037 0499 0556 1037 0668 1909 0036 0264 0072 0516 0009 0290 0179 0487 0364 0371 0343 0235 0035 0480 0560 0032 0217 0335 0218 0451 1928 1908 0579 0630 0661 1900 1668
Gorenje 0370 0421
GPM 0218
Gradiente 0053 0056 0392 0170 0037 0556
Graetz 0361 0371 0163 0037 0339 0556
Gran Prix 0648
Granada 0400 0037 0556 0226 0356 0359 0012 0045 0072 0146 0108 0208 0217 0036 0339 0516 0473 0335 0560 0047 0163 0363 0225 0343 0548
Grandin 0037 0556 0009 0163 0610 0714 0715 0668 0374 0320 0282 0218 0455 0400 0579 1037 1668
Gronic 0102 0217 0163
Grundig 0535 0195 0191 0554 0487 0070 0706 0037 0556 0587 0009 0036 0443 0370 0740 1935 1908 0630
Grunpy 0179 0180
Haaz 0706

<sub>154</sub>
Haier 0698 0869 0264
Halifax 0264 0216 0217
Hammerstein 0264 0060
Hampton 0216 0217
Hanimex 0218 0294 1908
Hanseatic 0037 0556 0499 0519 0349 0163 0361 0292 0544 0282 0394 0320 0634 0428 0370 0661 0009 0294 0217 0431 0087 0377 0714 0808
Hantarex 0009 0037 0556 0102 0516 0238
Hantor 0037 0556
Harley Davidson 0179
Harman/Kardon 0054 0078
Harsper 0865
Harvard 0068 0180
Harwood 0009 0412 0032 0037 0556 0487
Hauppauge 0037 0556
HCM 0009 0412 0037 0556 0217 0218 0418 0282 0264
Hedzon 0556 0037
Hema 0217 0009
Hemmermann 0349 0544
Hifivox 0501 0109 0196 0399 0198
Higashi 0216
Highline 0264 0037 0556
Hikona 0218
Hinari 0208 0037 0556 0009 0218 0036 0179 0163 0364 0355 0443 0487 0235 0294 0264 1908
Hisawa 0282 0218 0400 0455 0610 1908 0714
HiSense 0848 0208
Hit 0087
Hitachi 0225 0038 1225 0056 0349 0036 0151 0356 0044 0150 0108 0473 0163 0343 0578 0196 0198 0217 0227 0576 0032 0194 0516 0072 0481 0499 0037 0563 0145 0556 0109 0363 0548 0719 0634 0744 0178 1137 0105 0279 0492 1481 0016 0047 0359 0361 0512 0480 0165 1045 0629 1037
Hitachi Fujian 0108 0828 0150 0225 0576
Hitsu 0009 0455 0218 0610
HMV 0087 0193
Höher 0714
Home Electronics 0606

<sub>152</sub>
Hornyphon 0037 0556 0012
Hoshai 0218 0455 0282
Huanyu 0374 0216
Hygashi 0217 0216
Hyper 0009 0216 0217 0247
Hypersonic 0361
Hypson 0037 0556 0714 0715 1934 0264 0217 0282 0455 0400 0238 1908 0668 1668
Hyundai 0037 0803 0865 0556 0706 0753
Iberia 0037 0556
ICE 0264 0037 0371 0009 0556 0218 0217 0216
Ices 0218 0216
Icos 0012
Ict 0037 1137 0556
Imperial 0037 0163 0370 0074 0556 0630 0411 0361 0349 0418 0247 0196 0431 0531
Indiana 0037 0556
Ingelen 0487 0610 0714 0163 0361
Ingersoll 0009
Inno Hit 0009 0072 0037 0556 0218 0290 0217 0516 0247 0102 0282
Innovation 0519 0037 0556 0068
Interactive 0037 0556 0012 0087 0512 0275 0327 0163 0361 0370 0501 0109 0411
Interbuy 0009 0037 0264 0247 0068 0512 0556
Interfunk 0037 0556 0012 0087 0512 0275 0327 0163 0361 0370 0501 0109 0349 0247 0200
Internal 0037 0556 0499 0374 1909
International 0216
Intervision 0282 0217 0455 0037 0068 0371 0377 0519 0448 0486 0370 0394 0487 0218 0102 0431 0163 0264 0247 0009 0556
Irradio 0009 0037 0556 0218 0247 0290 0371
Isukai 0218 0037 0556 0282 0455
ITC 0217 0320
ITS 0037 0371 0218 0282 0264 0216 0009 0556

ITT 0163 0480 0349 0361 0473 0548 0567 0193 0346 0339 0208 0179 0544 0610
ITT Nokia 0361 0548 0163 0473 0480 0349 0346 0208 0179 0339 0567 0606 0610 0631 0363 0431
ITV 0264 0037 0556 0247 0284 0374
Janeil 0046
JBL 0054
Jean 0036
JEC 0035
JMB 0037 0499 0634 0374 0556 0443 1908
Jocel 0712
Jubilee 0556
JVC 0653 0053 0190 0036 0683 0192 0193 0371 0218 0606 0418 0093 1923
Kaisui 0218 0282 0037 0556 0216 0455 0217 0009
Kamp 0216
Kapsch 0163 0361 0206 0259 0104
Karcher 0037 0556 0421 0370 0610 0163 0282 0102 0264 0778 0714
Kathrein 0556 0037
Kawa 0371
Kawasho 0158 0216
Kaypani 0052
KB Aristocrat 0163
KEC 0180
Kendo 0610 0037 0556 0163 0519 0512 0370 0377 0363 0428 0411 0102 0235 0247 0362
Kennedy 0163 0206 0435
Kenwood 0019 0030 0105
KIC 0217 0329
Kingsley 0216
Kiota 0001
Kiton 0556 0037 0668 1668
Kloss 0024
Kneissel 0037 0385 0370 0610 0411 0374 0499 0556 0435 0259 0292 0238 0362 1908
Kolster 0037 0556 0102 0349 0247
Konichi 0009
Konka 0037 0707 0556 0632 0371 0628 0638 0714 0418 0703 0218 0725 0726 0641

FIG. 6C 0816 0587 0754 0779
Kontakt 0487
Korpel 0037 0556
Korting 0087 0421 0370 0320
Kosmos 0037 0556
Kotron 0412 0264
Koyoda 0009
Kraking 0238
Kriesler 0012
KTV 0030 0180 0185 0217 0280
Kuba 0349 0163
Kuba Electronic 0303 0349 0163
Kyoshu 0412 0418 0264 0032
Kyoto 0385 0032 0163 0216 0217
LaSAT 0486 0370
Leader 0009
Lecson 0037 0556
Legend 0009
Lemair 0411 0032
Lenco 0037 0009 0163 0374 0556 0104
Lenoir 0009
Lesa 0247
Levis Austria 0037 0556
Leyco 0264 0072 0037 0556 0294 0579
LG 0037 0056 0370 1178 0009 0377 0032 0001 0217 0002 0556 0714 0216 0431 0290 0163 0178 0606 0109 1934 1926 0698 0715 0823 0442
Liesenk & Tter 0327 0037 0556
Liesenkotter 0037 0327 0328 0012 0556
Lifetec 0037 0009 0519 0374 0668 0512 0655 1037 1137 0556 0218 0264 1668 0683
Lloyd's 0001 0009
Lloytron 0032
LME 0431
Loewe 0512 0037 0556 0655 0370 0633 0087 0292 0362 0790 0516
Logik 0011 0016 0033 0060 0698 0773 0009 0193 0264 0371 0001
Logix 0668 1668

/-154

Luma 0037 0363 0206 0305 0163 0411 0556 0374 0009 0362 0259
Lumatron 0363 0206 0305 0037 0556 0362 0163 0259 0361 0217 0264 0073
Lux May 0037 0009 0556 0581
Luxman 0056 0579
Luxor 0194 0290 0363 0480 0492 0349 0361 0208 0356 0548 0163 0346 0473 0179 0217 0631 1037
LXI 0047 0054 1347 0154 0156 0178
Madison 0037 0556
Magnadyne 0087 0247 0516 0102 0163 0544
Magnafon 0516 0102 0216 0073
Magnavox 0037 0054 0020 0556 0024 0028 0030 0036 0179 0187 0386 0780
Magnum 0648 0714 0037 0556 0715
Majestic 0016
Mandor 0264
Manesth 0037 0556 0235 0217 0264 0320 0035 0294 0163 0363
Manhattan 0037 0556 0668 1037 0163 0778 1668
Marantz 0037 0054 0030 0556 0412
Marelli 0087
Mark 0037 0556 0217 0216 0374 0009 0714 0715
Master's 0499
Masuda 0218 0371 0009 0264 0037 0217 0556
Materin 0858
Matsui 0037 0556 0487 0009 0235 0177 0011 0355 0072 0033 0036 0217 0354 0294 0371 0433 0443 0363 0579 0455 0163 0272 0349 0516 0035 0431 0208 0045 0195 0191 0335 0714 0544 1908 1037 0629
Matsushita 0250 0650
Matsuviama 0587
Maxam 0264
MCE 0009
Mediator 0037 0556 0012

/-152

Medion 0037 0668 0519 0512 0556 1137 0698 0808 1908 1037 1437 1900 1668
Megas 0610
Megatron 0003 0145 0178
MEI 0185 1037 0037 0556
Melectronic 0346 0037 0512 0109 0343 0247 0105 0104 0374 0009 0217 0480 0492 0216 0411 0349 0163 0287 0556 0634 0361 0191 0195 0068 0661
Melvox 0400
Memorex 0009 0016 0056 1920 0150 0154 0178 0250 0060 1924
Memphis 0337 0072 0009 0385
Mercury 0001 0037 0009 0556 0329
Metz 0195 0535 0447 0554 0191 0367 0388 0746 0037 0087 0556 0275 0587 0668 1037 1668
MGA 0019 0030 0150 0178 0037 0556 0218 0104
Micromaxx 0037 0556 0668 1037 0630 0808 1668
Microstar 0808
Midland 0017 0032 0047 0051 0135
Minato 0037 0556
Minerva 0487 0535 0195 0070 0191 0554 0516 0108 0150
Minoka 0412 0037 0556 0359
Mirror 1900
Mistral Electronics 0193
Mitsubishi 0019 0108 0150 0093 0512 0037 0178 0354 0087 0033 0036 0193 0535 0556 0208 1934 1037 1917
Mitsuri General 0163
Mivar 0292 0290 0291 0370 0216 0609 0516 0217
Monaco 0009
Morgan's 0037 0556
Motorola 0093
MTC 0019 0060 0370 0030 0349 0056 0512 0163 0216 0361 0448
MTEC 0272 0032
MTlogic 0714
Multibroad-cast 0193
Multistan-dard 0102

/-154

Multitec 0037 0556 0486 0668 1037 1668
Multitech 0180 0349 0009 0363 0486 0037 0370 0556 0217 0216 0247 0102 0264
Murphy 0104 0216 0072 0163
Musikland 0037 0218 0247 0556
Myryad 0556 0037
NAD 0156 0166 0178 0361 0163
Naiko 0037 0606 0556
Nakimura 0374 0037 0556
Naonis 0363 0163
NAT 0226 0340 0214
National 0214 0226 0340
NEC 0170 1170 1270 0036 0320 0019 0030 0056 0455 0497 0009 0374 0217 0037 0556 0011 0704 0603 0499 1704 0053 0661
Neckermann 0037 0191 0370 1505 1010 0200 0554 0556 0163 0327 0418 0349 0087 0247 0217 0411 0320 0363 0512
NEI 0037 0556 0337 0431 0371 0163
Nesco 0247 0179 1908
Netsat 0037 0556
Network 0032 0337
Neufunk 0037 0009 0556 0610 0218 0282 0714
New Tech 0037 0009 0556 0343 0217 0448
New World 0218
Nicamagic 0216
Nikkai 0072 0218 0037 0556 0217 0264 0032 0035 0337 0216 0009 0036
Nikko 0092 0178 0030
Nishi 0482
Noblex 0430
Nobliko 0102 0070 0216
Nogamatic 0399 0501 0109 0196
Nokia 0361 0163 0480 0349 0548 0492 0359 0473 0339 0208 0374 0631 0606 0346 0179 0320 0567 0610 0109 1912
Nordic 0217
Nordmende 0109 0714 0501 0287 0399 0196 0343 0198

/-152

FIG. 6D 0560 0195 0037 0556
0335 0163 0471
Norfolk 0163
Normerel 0037 0556
Noshi 0018
Novak 0012 0037 0556
Novatronic 0037 0105
0374 0531 0556
NTC 0092
NU-TEC 0455 0698
Nurnberg 0163 0361
Oceanic 0567 0163 0400
0361 0294 0208 0563
0473 0548 0480
Odeon 0264
Okano 0370 0037 0556
0264 0072 0009
Omega 0264
Omni 0780 0698 0826
Onwa 0180 0371 0602
0218 0433 0581 0102
0431
Opera 0037 0556
Optimus 0250 0650 0166
0154 1924
Optonica 0093 0165
Orbit 0037 0556
Orion 0037 0179 0236
0355 0463 0556 0655
0714 0235 0443 0294
0177 0320 0011 0009
0321 0364 0102 0264
0412 0516 0531 0544
1916 1908 0033 1905
Orline 0037 0218 0556
Ormond 0385 0668 1037
0037 0556 1668
Orsowe 0516
Osaki 0072 0218 0032
0217 0264 0493 0037
0412 0272 0374 0355
0556
Osio 0037 0556 0290
Oso 0218
Osume 0157 0072 0036
0032 0218 0037 0556
Otto Versand 1505 1010
0036 0093 0512 0037
0556 0535 0195 0544
0349 0554 0191 0361
0235 0109 0294 0226
0247 0303 0320 0217
0009 0282 0343 0428
0431 0516 0519
Pace 1908
Pacific 0037 0556 1137
0714 1037
Pael 0216

Palladium 0370 0037
0191 1505 1010 0200
0418 0554 0556 0247
0327 0349 0087 0163
0217 0411 0655 0519
0363 0630 0714 1137
Palsonic 0264 0412 0037
0284 0217 0377 0218
0698 0556 0448 0773
0779 0001 0418
Panama 0009 0217 0264
0216 0037 0556 0247
Panashiba 0001
Panasonic 0051 0650
0108 0250 1924 0226
0214 0361 0367 0340
0516 0037 0556 0163
0548 1210 1310 1930
0001 0853 1941 1946
Panavision 0037 0411
0556
Pathe Cinema 0163 0238
0216 0400 0320 0292
0349 0431 0370
Pathe Marconi 0501 0109
0196 0198 0399
Pausa 0009
Penney 0135 0747 0018
0019 0047
Perdio 0072 0320 0163
0037 0216 0282 0556
Perfekt 0037 0556
Pershin 0400
Phase 0032
Philco 0054 0087 0463
0020 0074 0028 0418
0145 0030 0019 0247
0163 0370 0037 0556
0186 0519
Philex 0193 0163
Philharmonic 0217
Philips 0054 0556 0037
0238 0012 0721 0554
0191 0087 0193 0423
0343 0570 0374 0000
0772 0009 0200 0080
Phoenix 0037 0556 0370
0486 0163 0087 0072
0216 0320 0385
Phonola 0037 0556 0012
0087 0193 0216 0080
Pilot 0019 0556 0030
0037 0712
Pioneer 0038 0166 0011
0037 0170 0556 0423
0428 0679 0370 0343
0361 0109 0163 0287
0486 0512 0760
Pionier 0370 0486
Plantron 0037 0556 0264
0009

Playsonic 0714 0037
0217 0339 0715
Policom 0102 0109 0196
0198 0206 0238 0275
0361 0163 0070 0074
0087 0501 0535
Polytron 0697 0282
Poppy 0009
Portland 0092 0374 0019
1909
Powerpoint 0487 0037
0556
Prandoni-Prince 0247
0516 0361 0363
Precision 0217
Premier 0009 0264
Prima 0032 0009 0264
0303 0068 0412
Princess 0698
Prinston 1037
Prinz 0072 0544 0349
0361 0194
Prism 0051
Profex 0009 0163 0431
0361 0363
Profi 0009
Profitronic 0037 0556
0102
Proline 0037 0556 0625
0634 0630 0411 0012
0321 0072 0621
Proscan 0047 1347 0030
Prosco 0156
Prosonic 0037 0556 0370
0374 0371 0668 0714
0451 0216 0214 0579
0217 1668
Protech 0037 0556 0217
0009 0247 0349 0102
0264 0431 0418 0337
0668 0282 0163 0486
1037 1668
Proton 0178 0466 0003
0052
Provision 0499 0037 0556
1037 0714
Pulsar 0017 0019
Pye 0037 0556 0012 0087
0554 0374 0349 0412
Pymi 0009
Quadra Vision 0400
Quadral 0218
Quasar 0247 0650 0250
0009 0051 1924
Quelle 0037 1505 1010
0011 0501 0109 0512
0535 0544 0349 0554
0191 0361 0032 0036
0217 0247 0074 0327
0328 0070 0104 0105
0668 0556 0157 0195
0200 0264

0290 0146 0294 0346
0421 0009 1668
Questa 0036 0032
R-Line 0037 0556 0163
Radialva 0109 0218 0431
0163 0037 0556 0287
0337
Radiola 0037 0556 0012
0217
Radiomarelli 0087 0516
0247 0037 0556
RadioShack 0019 0037
0030 0556 0032 0047
0056 0154 0165 0178
0180
Radiotone 0009 0037
0556 0428 0370 0579
0418 0412 0648 0668
0264 1037 1668
Rank 0070
Rank Arena 0036 0796
0157 0602 0753
RBM 0070
RCA 0047 0135 0174
0625 0018 0019 0038
0051 0093 0560 0335
0090 0343 0753
Realistic 0019 0030 0032
0056 0154 0165 0178
0180
Recor 0037 0418 0556
Rectiligne 0037 0556
Rediffusion 0361 0548
0036 0346
Redstar 0037 0556
Reflex 0037 0556 1037
0668 1668
Relisys 0865
Reoc 0714 0634 1909
Revox 0037 0556 0370
Rex 0305 0206 0363 0411
0247 0163 0259 0264
RFT 0087 0292 0370 0428
0072 0264 0037 0556
Rhapsody 0216 0185
Ricoh 0037 0556
Roadstar 1037 0009 0418
0037 0556 0668 0218
0264 0282 1916 1668
Robotron 0087
Rodex 0037 0556
Rowa 0264 0698 0217
0712 0009 0216 0587
Roxy 0448
Royal Lux 0421 0370
0412 0335
Rukopir 0556 0037
Runco 0017 0030
Saba 0625 0287 0087
0399 0163 0109 0501
0516 0343

FIG. 6E 0361 0498 0196 0198
0335 0548 0471 0560
0250 0714
Saccs 0238
Sagem 0610 0455 0282
Saisho 0235 0516 0177
0009 0011 0033 0217
0431 0163 0264 0354
0544
Saivod 0037 0556 0668
0712 1037 1668
Sakaï 0163
Sakyno 0455
Salora 0290 0194 0349
0163 0356 0359 0361
0364 0516 0363 0548
0339 0208 0480 0621
Salsa 0335
Sambers 0516 0102
Sampo 0030 0032 0052
Samsung 0019 0618 0056
0587 0037 0178 0030
0556 0009 0702 0093
0217 0448 0482 0370
0264 0329 0090 0216
0290 0644 0060 0032
0072 0208 0519 0163
0625 0812
Sandra 0216 0217
Sanela 0238
Sansei 0092 0451
Sansui 0037 0729 0556
0706 0371 0655 0727
0726 0725 0463 0602
0421 0455 0861
Santon 0009
Sanyo 0154 0208 0157
0484 0292 0721 0036
0011 0370 0339 0072
0216 0217 0104 0045
0555 0146 0009 0544
0163 0037 0108 0159
0556 0486 0799
Save 0037 0556
Saville 1908
SBR 0037 0556 0012 0193
Schaub Lorenz 0349 0548
0714 0606 0361 0486
0374
Schneider 1137 0037
0556 0519 0012 0303
0544 0349 0394 0259
0343 0217 0247 0371
0361 0218 0668 1037
0163 0648 0714 1909
1908 1668
Scimitsu 0019
Scotland 0163
Scott 0236 0178 0179
0180 0019
Sears 0047 0146 0054
0156 0747 0154 0056
0159 0171 0178 0179

— 152

Seaway 0634
Seelver 0556 1037 0037
SEG 0037 0556 1037 1437
0668 0217 0487 0009
0349 0163 0264 0634
0036 0102 0247 0362
0216 0218 1909 1668
1901
SEI 0087 0102 1505 1010
0163 0516 0544 0349
0294 0206 0037 0556
0177
Sei-Sinudyne 0102 0206
0294 0516 1505 1010
0544 0037 0556 0087
Seleco 0305 0206 0363
0259 0362 0163 0411
0371 0036 0264 0346
0435
Semivox 0180
Semp 0156
Sencora 0009
Sentra 0035 0218 0009
0349
Serino 0610 0455 0216
0093
Sharp 0093 0165 0386
1193 0157 0036 0294
0491 0653 0053 0256
0193 0186 0516 0200
0760 0818 1917
Shintoshi 0037 0556
Shivaki 0037 0556 0443
0451 0374 0178
Shogun 0019
Shorai 0294 0179
Show 0418 0009 0072
Siarem 0163 0087 0102
0516
Siemens 0191 0535 0554
0200 0195 0327 0328
0157 0032 0146 0037
0556 0361
Siera 0037 0556 0012
0587
Siesta 0370
Silva 0037 0556 0216
0361 0648
Silver 0036 0037 0455
0361 0556 0179 0715
0163
Simpson 0186 0187
Singer 0009 1537 0087
0806 0037 0556 0102
0247 0435 0400 0567
0335 0163
Sinotec 0773
Sinudyne 0177 0087
0235 0102 0294 0163
0361 0516 0544 0349
1505 1010 0206 0037
0556 1908
Skantic 0356
Sky 0037 0282 0556
Skymaster 0105
Skysonic 0696 0753
SLX 0668 1668
Smaragd 0487

— 152

Soemtron 0865
Sogera 0320
Solavox 0032 0361 0072
0163 0548 0037 0556
Sonawa 0218
Soniko 0037 0556
Sonitron 0208 0370 0339
0217
Sonneclair 0037 0556
Sonoko 0037 0556 0009
0264 0282 0217
Sonolor 0208 0567 0163
0400 1505 1010 0548
0361 0282
Sontec 0037 0556 0370
0294 0009
Sony 1505 1651 1010
0011 0000 0036 0102
0353 0111 0037 0080
0556 0157 1925 0834
Sound & Vision 0102
0218 0374 0037 0556
Soundesign 0178 0179
0180 0186
Soundwave 0037 0556
0320 0418 0032 0715
Spectra 0009
Ssangyong 0032 0009
SSS 0019
Stag 0032
Staksonic 0009
Standard 0037 0556 1037
0218 0009 0217 0320
0374
Starlite 0009 0163 0037
0556 0264 0412
Stenway 0282 0218
Stern 0305 0206 0259
0163 0363 0264 0411
0435
Strato 0037 0556 0264
0009
Stylandia 0217
Sunic Line 0037 0556
Sunkai 0294 0355 0321
0455 0218 0235 0610
0037 0556 0487 0531
Sunstar 0371 0037 0556
0009 0579 0264
Sunwood 0037 0556
0009
Superla 0516 0216 0217
Supersonic 0208 0556
0698 0264 0805
SuperTech 0009 0037
0556 0216 0218
Superton 0431
Supra 0178 0374 0009
0056
Susumu 0335 0218 0287
Sutron 0009

— 154

Swissline 0247
Sydney 0216 0217
Sylvania 0054 0186 0020
0028 0030
Symphonic 0171 1904
Sysline 0037 0556
Sytong 0216
T+A 0447
Tactus 0272
Tandberg 0367 0411
0109 0337 0196 0362
0361 0163
Tandy 0218 0072 0217
0247 0093 0163
Targa 0702
Tashiko 0036 0217 0146
0170 0032 0216 0359
0163 0363
Tatung 0003 0037 0556
0072 0516 0217 0272
0011 0629 0621 0033
1908
TCM 0714
Teac 0698 0512 0037
1437 1037 0556 0712
0668 0455 0217 0706
0264 0544 1909 0686
0178 0009 0171 0412
0349 0721 0282 0418
0431 0755 0170 0714
1932 1668 1913 1949
1724
TEC 0217 0009 0247 0471
0335 0337 0259 0037
0556 0361 0163
Tech Line 0037 0556 0668
1437 1668
Techica 0218
Technema 0320
Technics 0250 0051
TechniSat 0655 0037
0556 0163
Technol Ace 0179
Techwood 0003 0051
0056
Tecnimagen 0556
Tedelex 0217 0418 0606
1537 0009 0706 0208
0698 0587 0037 0284
0556 0431
Teiron 0009
Teknika 0054 0092 0019
0060 0179 0180 0186
0016
Teleavia 0109 0501 0287
0196 0399 0343
Telecor 0037 0556 0163
0218 0217 0259 0284
0394
Telefunken 0056 0109
0625 0702 0501 0587
0698 0498 0712 0471
0820 0399 0287 0074
0101 0335 0262 0073
0343 0196 0037 0556
0486

Telefusion 0037 0556
Telegazi 0037 0163 0259
0218 0264 0284 0556
Telemeister 0320 0037
0556
Telesonic 0037 0556
Telestar 0009 0037 0556
0579 0412
Teletech 0037 0556 0668
0009 0247 0337 1037
1668
Teleton 0217 0275 0206
0163 0349 0259 0186
0036 0363
Televideon 0320 0163
0216
Teleview 0037 0556
Televiso 0400
Telexa 0102
Temco 0294
Tempest 0009 0037 0556
0264
Tennessee 0037 0556
Tensai 0104 0218 0037
0556 0217 0294 0320
0009 0105 0374 0371
0377 0247 0715 0163
Tenson 0320 0009
Tesla 0037
Tevion 0519 0037 0556
0648 0668 1137 0714
1037 1668
Texet 0217 0374 0009
0216 0218
Thomas 1904
Thomson 0625 0560 0287
0109 0501 0399 0471
0335 0196 0198 0343
0037 0556 0574 1447
0349
Thorn 0108 0193 0109
0073 0225 0343 0190
0361 0238 1505 0192
1010 0074 0499 0535
0037 0072 0556 0011
0104 0012 0335 0512
0033 0359 0036 0272
0045 0374 0035 0070
0101 0356 0501
Thorn-Ferguson 0104
0108 0109 0190 0192
0238 0193 0361 0335
0499 0073 0035
TMK 0056 0178 0177
Tobishi 0218
Tokai 0072 0037 0556
0337 0668 0448 0163
0217 0374 0009 1037
1668
Tokaido 1037
Tokyo 0216 0035 0448
0329 0303
Tomashi 0282 0218
Tongtel 0780

Toshiba 0035 0060 0154
0508 0156 0243 0036
0070 0102 1508 0217
0109 0718 0195 0191
0618 1916 1908 0009
0698 0037 1945
Tosonic 0185
Towada 0349 0102 0217
Toyoda 0009 0371 0493
0264
Trakton 0009 0264 0217
Trans Continens 0668
0217 1037 0037 1668
0556 0486
TRANS-continents 0621
Transonic 0037 0556
0455 0587 0512 0264
0698 0712 0418 0009
Transtec 0216
Triad 0037 0556
Trical 0157
Trident 0516 0217
Tristar 0264 0218 0193
Triumph 0177 0516 0346
0556 0037 0243
Tsoschi 0282
TVTEXT 95 0556
Uher 0037 0556 0206
0320 0303 0374 0418
0486 0370 0259 0480
Ultra 0192
Ultravox 0087 0102 0374
0247 0216 0163 0037
0556
Unic Line 0037 0556 0473
0455 0349
United 0037 0556 0714
0715
Universal 0027 0037
0556
Universum 0346 0105
0535 0195 0473 0361
0247 0492 0480 0370
0200 0418 0011 0146
0512 0294 0036 0157
0032 0070 0163 0264
0104 0037 0556 0421
0411 0290 0074 0327
0328 1505 1010 0668
0544 0349 0217 0501
0109 0362 0337 0177
0631 0554 0009 1901
1037 1437 0170 1668
Univox 0037 0556 0337
0087 0163 0238
Utax 0163
V7 Videoseven 1755
Vestel 0037 0163 0217
0556 0668 1037 1668
Vexa 0009 0037 0556
Vibrant 0272
Victor 0053
Videologic 0218 0216

Videologique 0216 0218
0217
Videosat 0247
VideoSystem 0037 0556
Videotechnic 0216 0320
0217 0374
Videoton 0356 0163 0431
Vidikron 0102
Vidtech 0019 0036 0178
Viking 0046
Viper 0337
Visiola 0216
Vision 0032 0037 0264
0556 0320 0217
Vistar 0206 0361 0567
Vortec 0037 0556
Voxson 0087 0037 0556
0363 0418 0163 0178
Waltham 0217 0356 0418
0287 0385 0037 0556
0668 0109 1037 0431
1668
Wards 0165 0179 0016
0019 0027
Watson 0037 0556 0320
0163 0218 0305 0579
0519 0394 0009 0668
1037 1908 1437 1668
Watt Radio 0102 0544
0349 0163 0216
Wega 0037 0556 0036
0087
Wegavox 0009 0037 0556
Weltblick 0037 0556 0320
0217
Welttech 0284
Weston 0037 0556
Wharfedale 0037 0861
0519 0556
White Westing-house
0320 0216 0037 0556
0337 1909
Windsor 0668 1037 1668
Windstar 0282 0337
Windy Sam 0556
Wintel 0714
Worldview 0455
Xenius 0634
XLogic 0698 0860
Xrypton 0037 0556
Yamaha 0019 0650 0030
Yamishi 0282 0455 0218
0037 0556 0217
Yokan 0037 0556
Yoko 0217 0037 0556
0218 0264 0009 0431
0421 0370 0305 0339
0216 0247
Yorx 0218
Zanela 0238

Zanussi 0206 0305 0363
0217
Zenith 0017 0016 0092
1909
Zenor 0339
Zonda 0003
ZX 0284 1908

FIG. 6G

Pin 1   Bed Monitoring Status On
Pin 2   Read Light
Pin 3   Room Light
Pin 4   Speaker High
Pin 5   Potentiometer Wiper
Pin 6   Bed Exit Status On
Pin 7   Nurse Call Interlock
Pin 8   Audio Transfer -
Pin 9   Audio Transfer +
Pin 10  Interlock +
Pin 11  Interlock -
Pin 12  Bed Monitoring Fowler 30 deg. Alert
Pin 13  No Connect
Pin 14  Potentiometer Low Common
Pin 15  Potentiometer High Common (Std.) / Audio (STV)
Pin 16  Nurse Answer Light +
Pin 17  Bed Monitor Alert
Pin 18  Bed Monitoring Siderail Alert
Pin 19  Nurse Call Light +
Pin 20  No Connect
Pin 21  No Connect
Pin 22  No Connect
Pin 23  Brake Status On
Pin 24  No Connect
Pin 25  Nurse Call +
Pin 26  Nurse Call NO/NC
Pin 27  Room/Read Light Common
Pin 28  Nurse Call Light -
Pin 29  Nurse Answer Light -
Pin 30  Priority NO/NC
Pin 31  Priority Common
Pin 32  Bed Monitoring Low Height Alert
Pin 33  TV - (Std.) / Data (STV)
Pin 34  TV + (Std.) / Common (STV)
Pin 35  Speaker Low Common
Pin 36  Audio Shield
Pin 37  Bed Monitoring Common FIG. 7
(Prior Art)

PATIENT SUPPORT APPARATUS SYSTEMS WITH TELEVISION DETECTION

CROSS-REFERENCE TO RELATED APPLICATIONS

This application claims priority to U.S. provisional patent application Ser. No. 63/244,768 filed Sep. 16, 2021, by inventors Jerald Trepanier et al. and entitled PATIENT SUPPORT APPARATUS SYSTEMS WITH TELEVISION DETECTION, the complete disclosure of which is incorporated herein by reference.

BACKGROUND

The present disclosure relates to patient support apparatuses, such as beds, cots, stretchers, recliners, or the like, that are adapted to communicate with an existing nurse call system and a television.

Existing hospital beds often include an exit detection system that detects when the patient leaves the bed and notifies a nurse call system that the patient has left the bed. Existing hospital beds also often include a nurse call button and speaker/microphone that allow the patient to communicate with a remote nurse using the nurse call system. Still further, hospital beds also typically include a user interface (which may be a removable pendant or a control panel built into the bed) that allows the patient to remotely control a television positioned within the same room as the hospital bed. In order for the user interface to properly control the television, the user interface needs to know what type (e.g. brand or model) of television it is controlling so that the proper remote control signals can be sent to the particular type of television that is installed in a particular room.

SUMMARY

According to various aspects, the present disclosure provides an improved patient support apparatus and/or headwall unit that automatically detects the type of television that is installed within a room, and then automatically adjusts the signals that are sent to the television so that the control signals have the proper format/sequence for controlling the particular type of television within that room. This automatic television-type detection eliminates the need for a technician, or other individual, to manually instruct the user interface what type of television is installed within a particular room, thereby reducing the labor of installing a patient support apparatus in a particular room and ensuring its compatibility with the particular television installed within that particular room. In some aspects, the patient support apparatus itself detects the television type automatically. In other aspects, a headwall unit attached to a headwall of the room automatically detects the television type. In still other aspects, both the patient support apparatus and the headwall unit may be configured to automatically detect the television type. The automatic detection of the television type is carried out by one or more infrared sensors that are built into the patient support apparatus and/or the headwall unit. These infrared sensors are used for carrying out infrared communication between the patient support apparatus and the headwall unit, in addition to (at least one of them) being used to detect the type of television that is positioned within that room.

According to a first aspect of the present disclosure, a headwall unit is provided that is adapted to be mounted to a headwall of a room in a healthcare facility. The headwall unit includes an outlet interface, a first infrared transceiver, and a controller. The outlet interface is adapted to electrically couple to a wall outlet mounted in the headwall. The outlet interface includes a set of pins adapted to electrically couple to a plurality of conductors defined in the wall outlet when the outlet interface is coupled to the wall outlet. At least one pin of the set of pins is a television control pin adapted to electrically couple to a television control conductor defined in the wall outlet. The first infrared transceiver is adapted to wirelessly communicate with a second infrared transceiver positioned onboard a patient support apparatus when the patient support apparatus is positioned adjacent to the headwall unit. The controller is adapted to analyze signals detected by the first infrared transceiver to determine if the signals were emitted by a television remote control, and, if so, to determine a type of television that the television remote control is adapted to control, and to forward a television control message to the television control pin in response to receipt of a television command from the patient support apparatus.

According to another aspect of the present disclosure, a headwall unit is provided that is adapted to be mounted to a headwall of a room in a healthcare facility. The headwall unit includes an outlet interface, a first RF transceiver, an infrared receiver, and a controller. The outlet interface is adapted to electrically couple to a wall outlet mounted in the headwall and includes a set of pins adapted to electrically couple to a plurality of conductors defined in the wall outlet when the outlet interface is coupled to the wall outlet. At least one pin of the set of pins is a television control pin adapted to electrically couple to a television control conductor defined in the wall outlet. The first RF transceiver is adapted to wirelessly communicate with a second RF transceiver positioned onboard a patient support apparatus positioned adjacent to the headwall unit. The infrared receiver is adapted to receive signals from a television remote control, and the controller is adapted to determine a type of television the television remote control is adapted to control based on an analysis of the signals. The controller is further adapted to generate a television control message based on the type of television, and to forward the television control message to the television control pin in response to receipt of a television command from the patient support apparatus.

According to another aspect of the present disclosure, the controller is further adapted to determine the type of television that the television remote control is adapted to control by analyzing a header within a packet sent by the television remote control.

In some aspects, the first RF transceiver is adapted to receive the television command from the patient support apparatus.

The type of television, in some aspects, includes a brand and/or model of the television.

The controller, in some aspects, is adapted to change the television control message based on the type of television and based on the television command received from the patient support apparatus.

The television command may include a channel changing command, a volume changing command, a closed-captioning command, or a power command.

The first infrared transceiver, in some aspects, is further adapted to transmit a unique identifier to the patient support apparatus, wherein the unique identifier differentiates the headwall unit from other headwall units positioned within the healthcare facility.

The controller, in some aspects, is further adapted to receive an exit detection signal from the patient support apparatus via the first RF transceiver and to change a voltage on a particular pin of the set of pins in response to receipt of the exit detection signal.

In some aspects, at least one pin of the set of pins is an audio pin and the controller is adapted to receive a plurality of audio signals from the television via the audio pin. The controller may further be adapted to transmit the audio signals to the patient support apparatus via the first RF transceiver.

According to some aspects, the infrared receiver is part of an infrared transceiver, and the infrared transceiver is adapted to transmit a unique identifier to the patient support apparatus, the unique identifier differentiating the headwall unit from other headwall units positioned within the healthcare facility.

According to another aspect of the present disclosure, a patient support apparatus is provided that includes a support surface, a cable interface, an infrared receiver, and a controller. The support surface is adapted to support a patient thereon. The cable interface is adapted to electrically couple to a nurse call cable and includes a set of pins adapted to electrically couple to a plurality of conductors defined in the cable. The set of pins includes a television control pin. The infrared receiver is adapted to receive signals from a television remote control. The controller is adapted to determine a type of television the television remote control is adapted to control based on an analysis of the signals, to generate a television control message based on the type of television, and to forward the television control message to the television control pin in response to receipt of a television command from a user interface onboard the patient support apparatus.

According to another aspect of the present disclosure, a patient support apparatus is provided that includes a support surface, a first infrared transceiver, and a controller. The support surface is adapted to support a patient thereon. The first infrared transceiver is adapted to communicate with a second infrared transceiver incorporated into a headwall unit adapted to be mounted to a headwall of a room in a healthcare facility. The controller is adapted to analyze signals detected by the first infrared transceiver to determine if the signals were emitted by a television remote control, and, if so, to determine a type of television that the television remote control is adapted to control. The controller is further adapted to forward a television control message to the headwall unit in response to receipt of a television command from a user interface onboard the patient support apparatus.

According to still another aspect of the present disclosure, a patient support apparatus is provided that includes a support surface, an RF transceiver an infrared receiver, and a controller. The support surface is adapted to support a patient thereon. The RF transceiver is adapted to communicate with a headwall unit adapted to be mounted to a headwall of a room in a healthcare facility. The infrared receiver is adapted to receive signals from a television remote control. The controller is adapted to determine a type of television the television remote control is adapted to control based on an analysis of the signals, to generate a television control message based on the type of television, and to forward the television control message to the headwall unit in response to receipt of a television command from a user interface onboard the patient support apparatus.

According to still other aspects of the present disclosure, the controller is further adapted to determine the type of television that the television remote control is adapted to control by analyzing a header within a packet sent by the television remote control.

The first RF transceiver, in some aspects, is adapted to wirelessly communicate with a second RF transceiver positioned onboard a headwall unit adapted to be mounted to a headwall of a room in a healthcare facility.

The controller, according to some aspects, is further adapted to forward the television control message to the headwall unit via the first RF transceiver.

In some aspects, the type of television includes a brand and/or model of the television.

The controller, in some aspects, is adapted to change the television control message based on the type of television and based on the television command received from the user interface.

The television command may be one of a channel changing command, a volume changing command, a closed-captioning command, or a power command.

In some aspects, the infrared receiver is further adapted to receive a unique identifier from a headwall unit adapted to be mounted to a headwall of a room in a healthcare facility. The unique identifier differentiates the headwall unit from other headwall units positioned within the healthcare facility.

In some aspects, the patient support apparatus further includes an exit detection system adapted to detect when a patient exits the patient support apparatus, and the controller is further adapted to change a voltage on at least one pin of the set of pins of the cable interface in response to the exit detection system detecting the patient exiting the patient support apparatus.

In some aspects, the RF transceiver is further adapted to receive a plurality of audio signals from the television and to route the audio signals to a speaker onboard the patient support apparatus.

Before the various aspects disclosed herein are explained in detail, it is to be understood that the claims are not to be limited to the details of operation or to the details of construction and the arrangement of the components set forth in the following description or illustrated in the drawings. The aspects described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various aspects. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 6A is a first portion of a table illustrating television identification codes for different brands of televisions;

FIG. 6B is a second portion of the table of FIG. 6A illustrating television identification codes for different brands of televisions;

FIG. 6C is a third portion of the table of FIG. 6A illustrating television identification codes for different brands of televisions;

FIG. 6D is a fourth portion of the table of FIG. 6A illustrating television identification codes for different brands of televisions;

FIG. 6E is a fifth portion of the table of FIG. 6A illustrating television identification codes for different brands of televisions;

FIG. 6F is a sixth portion of the table of FIG. 6A illustrating television identification codes for different brands of televisions;

FIG. 6G is a seventh portion of the table of FIG. 6A illustrating television identification codes for different brands of televisions; and FIG. 7 is a chart of a prior art example of the functions of the pins of a 37-pin cable often used in existing healthcare facilities.

DETAILED DESCRIPTION OF THE DISCLOSURE

Figure 1:
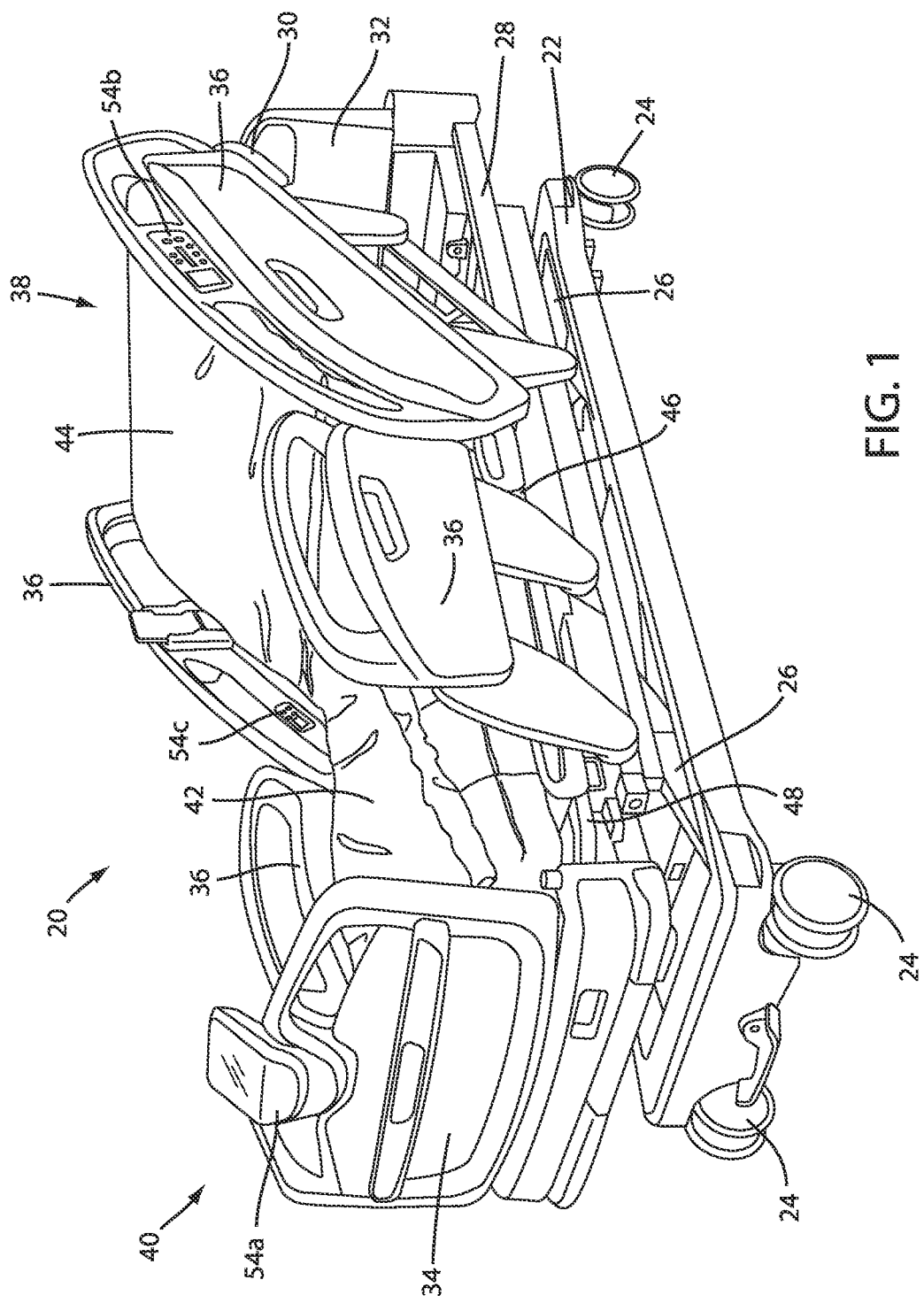
FIG. 1 is a perspective view of a patient support apparatus according to a first aspect of the present disclosure.

An illustrative patient support apparatus 20 according to a first aspect of the present disclosure is shown in FIG. 1. Although the particular form of patient support apparatus 20 illustrated in FIG. 1 is a bed adapted for use in a hospital or other medical setting, it will be understood that patient support apparatus 20 could, in different aspects, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated aspect, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon.

Support deck 30 is made of a plurality of sections, some of which are pivotable about generally horizontal pivot axes. In the aspect shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some aspects, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another aspect, the mechanical construction of patient support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Figure 2:
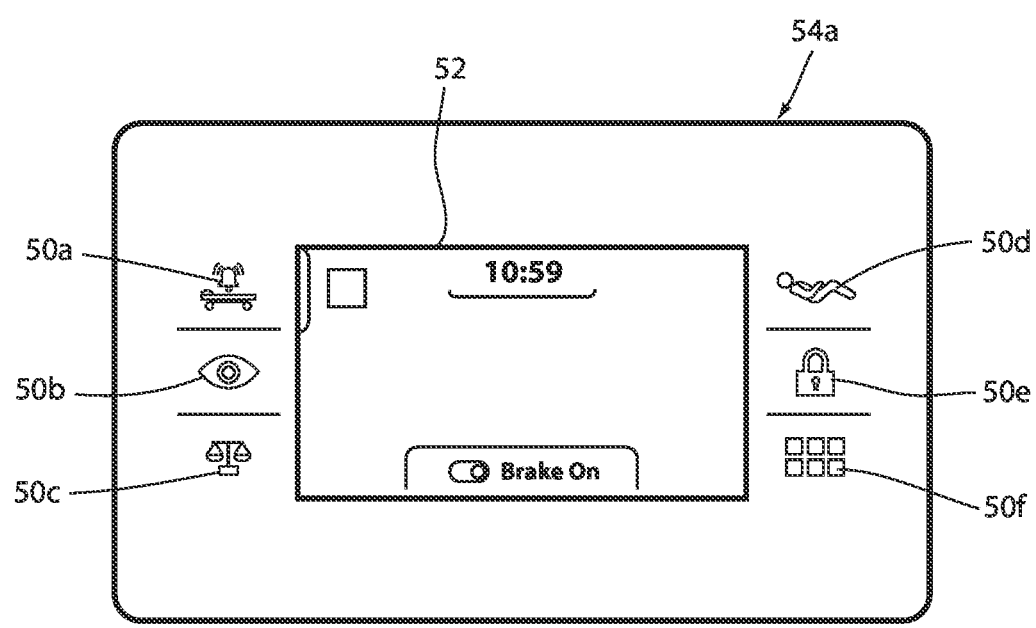
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the aspect shown in FIG. 1, patient support apparatus 20 includes a footboard control panel 54a, a pair of outer siderail control panels 54b (only one of which is visible), and a pair of inner siderail control panels 54c (only one of which is visible). Footboard control panel 54a and outer siderail control panels 54b are intended to be used by caregivers, or other authorized personnel, while inner siderail control panels 54c are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54a allow a user to control one or more of the following: change a height of support deck 30, raise or lower head section 44, activate and deactivate a brake for wheels 24, arm and disarm an exit detection system and, as will be explained in greater detail below, communicate with the particular IT infrastructure installed in the healthcare facility in which patient support apparatus 20 is positioned. One or both of the inner siderail control panels 54c also include at least one control that enables a patient to call a remotely located nurse (or other caregiver). In addition to the nurse call control, one or both of the inner siderail control panels 54c also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54c include, but are not limited to, the volume, the channel, the closed-captioning, and/or the power state of the television. With respect to the room and/or night lights, the features that may be controlled by one or more controls 50 on control panel 54c include the on/off state and/or the brightness level of these lights.

Control panel 54a includes a display 52 (FIG. 2) configured to display a plurality of different screens thereon. Surrounding display 52 are a plurality of navigation controls 50a-f that, when activated, cause the display 52 to display different screens on display 52. More specifically, when a user presses navigation control 50a, control panel 54a displays an exit detection control screen on display 52 that includes one or more icons that, when touched, control an onboard exit detection system. The exit detection system is adapted to issue an alert when a patient exits from patient support apparatus 20. Such an exit detection system may include any of the same features and/or functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference.

When a user pressed navigation control 50b (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses navigation control 50c, control panel 54a displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference.

When a user presses navigation control 50d, control panel 54 displays a motion control screen that includes a plurality of control icons that, when touched, control the movement of various components of patient support apparatus 20, such as, but not limited to, the height of litter frame 28 and the pivoting of head section 44. In some aspects, the motion control screen displayed on display 52 in response to pressing control 50d may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

When a user presses navigation control 50e, control panel 54a displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses on navigation control 50f, control panel 54a displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

For all of the navigation controls 50a-f (FIG. 2), screens other than the ones specifically mentioned above may be displayed on display 52 in other aspects of patient support apparatus 20 in response to a user pressing these controls. Thus, it will be understood that the specific screens mentioned above are merely representative of the types of screens that are displayable on display 52 in response to a user pressing on one or more of navigation controls 50a-f. It will also be understood that, although navigation controls 50a-f have all been illustrated in the accompanying drawings as dedicated controls that are positioned adjacent display 52, any one or more of these controls 50a-f controls alternatively be touchscreen controls that are displayed at one or more locations on display 52. Still further, although controls 50a-f have been shown herein as buttons, it will be understood that any of controls 50a-f could also, or alternatively, be switches, dials, or other types of non-button controls.

Figure 3:
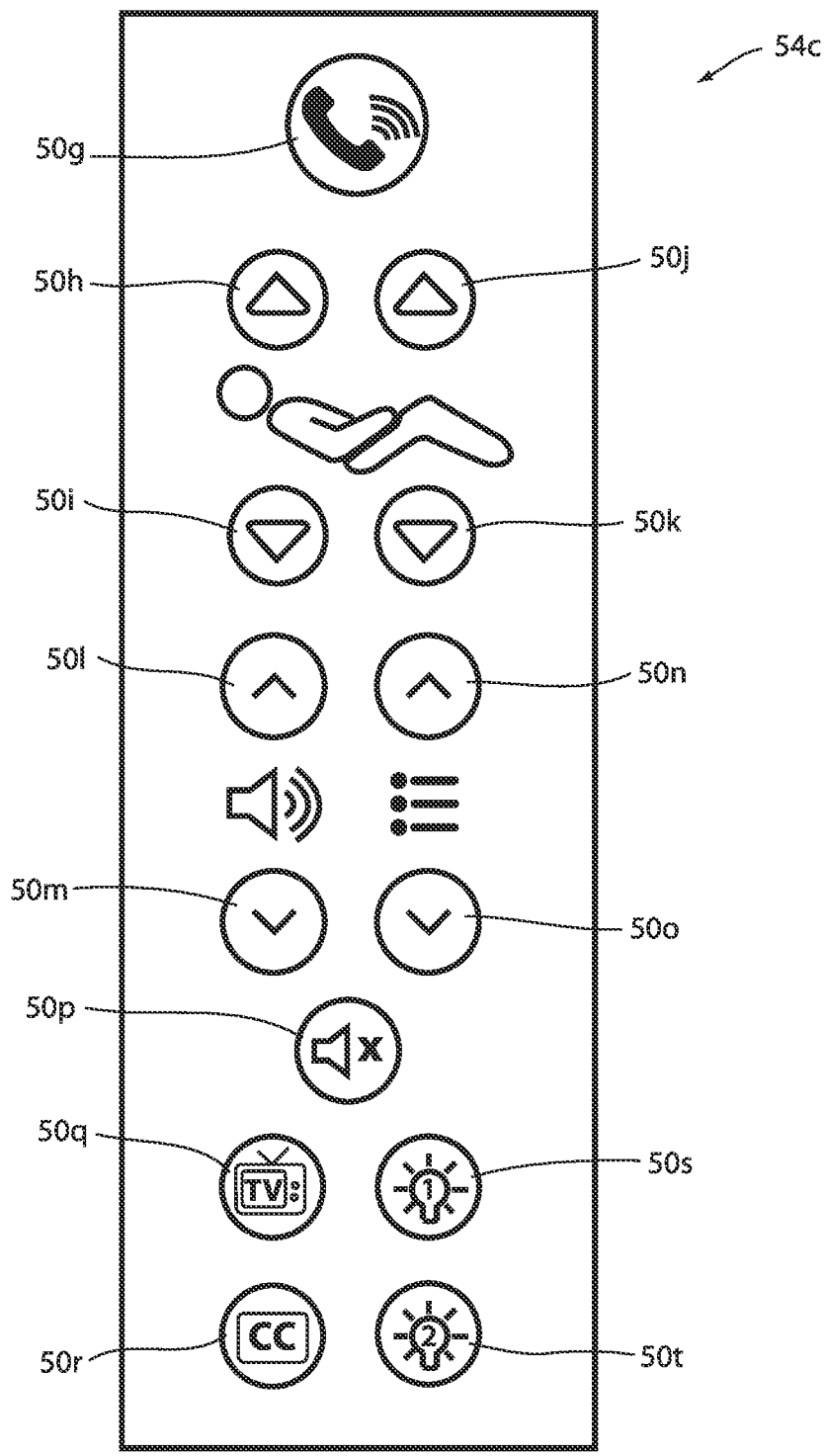
FIG. 3 is a plan view of an illustrative patient control panel of the patient support apparatus.

FIG. 3 illustrates one example of a patient control panel 54c that may be incorporated into patient support apparatus 20 and positioned at a location on patient support apparatus 20 that is convenient for a patient to access while supported on support deck 30, such as on an interior side of one of the siderails 36. Control panel 54c includes a plurality of controls 50g-t that are intended to be operated by a patient. A nurse call control 50g, when pressed by the patient, sends a signal to a nurse call system requesting that a remotely positioned nurse talk to the patient. A Fowler-up control 50h, when pressed by the patient, causes a motorized actuator onboard patient support apparatus 20 to raise Fowler section 44 upwardly. A Fowler-down control 50i, when pressed by the patient, causes the motorized actuator to lower Fowler section 44 downwardly. A gatch-up control 50j, when pressed by the patient, causes another motorized actuator to raise a knee section of support deck 30, while a gatch-down control 50k causes the motorized actuator to lower the knee section of support deck 30.

A volume-up control 50l, when pressed by the patient, causes patient support apparatus 20 to send a signal to an in-room television instructing it to increase its volume, while a volume down control 50m, when pressed, causes patient support apparatus 20 to send a signal to the television instructing it to decrease its volume. A channel-up control 50n, when pressed by the patient, causes patient support apparatus 20 to send a signal to the television instructing it to increase the channel number, while a channel-down control 50o, when pressed, causes patient support apparatus 20 to send a signal to the television instructing it to decrease the channel number.

A mute control 50p, when pressed, causes patient support apparatus 20 to send a signal to the television instructing it to either mute itself or unmute itself, depending upon whether the television is currently muted or unmuted. In other words, mute control 50p is a toggle control that alternatingly sends mute and unmute commands to the television when it is pressed.

Power control 50q is a toggle control that, when pressed, sends a signal to the television to either turn on or turn off, depending upon the television's current power status. Closed-captioning control 50r is another toggle control that, when pressed, sends a signal to the television to either turn on its closed-captioning feature or to turn off its closed captioning feature, depending upon whether the closed-captioning feature is currently on or off.

Control 50s is a toggle control that, when pressed, sends a signal to a first light to either turn on or turn off, depending upon the current state of that first light. Control 50t is another toggle control that, when pressed, sends a signal to a second light to either turn on or turn off, depending upon the current state of that second light. In some aspects, the first light is a reading light and the second light is a room light, both of which are positioned off-board the patient support apparatus 20.

It will be understood that not only the number of controls 50 on control panel 54c, but also the functions of the controls 50 on control panel 54c, the layout of the controls 50 on control panel 54c, and/or other aspects of control panel 54c may be modified from what is shown in FIG. 3. In some aspects, control panel 54c is implemented on a pendant controller that includes a cable that is plugged into a port on patient support apparatus 20. Still other manners of implementing control panel 54c are also possible.

Figure 4:
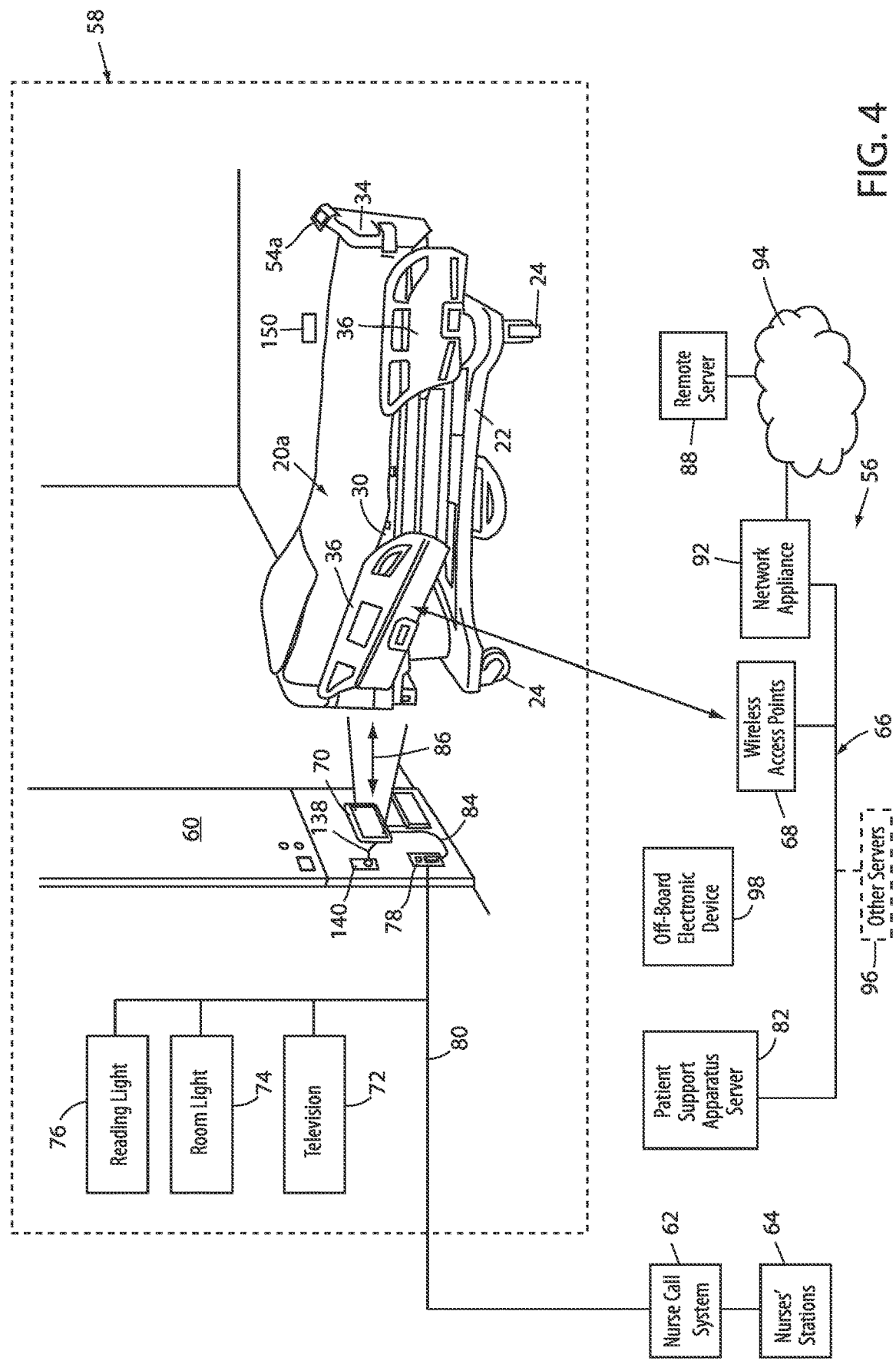
FIG. 4 is a diagram of the patient support apparatus shown wirelessly coupled to the IT infrastructure of a healthcare facility.

FIG. 4 illustrates patient support apparatus 20 positioned in a typical room 58 of a conventional healthcare facility 56. As shown therein, healthcare facility 56 includes a headwall 60, a nurse call system 62, one or more nurses' stations 64, a local area network 66, one or more wireless access points 68, a headwall unit 70, a television 72, a room light 74, a reading light 76, a communications outlet 78, and a plurality of conductors 80 that couple outlet 78 to various devices (e.g. television 72, room light 74, reading light 78, and nurse call system 78). It will be understood by those skilled in the art, however, that the healthcare facility infrastructure shown in FIG. 4 may vary widely from healthcare facility to healthcare facility.

As is shown in FIG. 4, patient support apparatus 20 is adapted to be communicatively coupled to the wall outlet 78 on headwall 60 by way of a wireless communication link 86 that wirelessly couples patient support apparatus 20 to a wireless headwall unit 70. Headwall unit 70, in turn, is coupled by way of a cable 84 to wall outlet 78. Headwall unit 70 and patient support apparatus 20 are able to communicate wirelessly with each other in a bidirectional fashion. That is, messages can be wirelessly sent from patient support apparatus 20 to headwall unit 70, and messages can be wirelessly sent from headwall unit 70 to patient support apparatus 20.

Although not shown in FIG. 4, patient support apparatus 20 may further be configured to be able to communicate with wall outlet 78 via a cable, if desired. When such wired communication is desired, nurse call cable 84 is connected directly from patient support apparatus 20 to wall outlet 78.

Wall outlet 78 is coupled to one or conductors 80 that electrically couple the wall outlet 78 to nurse call system 62 and to one or more other devices, such as television 72, room light 74, and/or reading light 76. Conductors 80 are typically located behind headwall 60 and not visible. In some healthcare facilities, conductors 80 may first couple to a room interface board that includes one or more electrical connections electrically coupling the room interface board to television 72 and/or nurse call system 62. Still other communicative arrangements for coupling wall outlet 78 to nurse call system 62 and television 72 are possible.

Communication link 86 (FIG. 4) enables patient support apparatus 20 to communicate with nurse call system 62, television 72, room light 74, and/or reading light 76. A patient supported on patient support apparatus 20 who activates a nurse call control on patient support apparatus 20 causes a signal to be conveyed wirelessly via communication link 86 to headwall unit 70, which in turn sends a wired signal along cable 84 to outlet 78, which in turn then sends a wired signal along one or more conductors 80 to the nurse call system 62, which then sends a notification to one or more remotely located nurses (e.g. nurses at one of the nurses' stations 64). If the patient uses a TV control positioned on one of the control panels (e.g. controls 50i-50r of control panel 54c; see FIG. 3) to change a channel or change the volume of television 72, the control conveys a signal in the same manner to television 72. That is, a wireless signal is sent from patient support apparatus 20 to headwall unit 70 via link 86, and headwall unit 70 responds to the signal by forward a television command signal to a particular pin of communication outlet 78 (via cable 84), and that particular pin of outlet 78 is in electrical communication with television 72 via one or more conductors 80. A similar signal path is followed when the patient uses a room light or reading light control on one of the control panels, except such signals are forwarded to different pins of outlet 78 that are in communication via conductors 80 with room light 74 and reading light 78, respectively. The patient is therefore able to control television 72, room light 74 and reading light 76 from patient support apparatus 20.

In addition to pins for communicating signals to television 72, room light 74, and reading light 76, outlet 78 typically includes a plurality of additional pins (often 37 pins total) that are used for other communications between patient support apparatus 20 and nurse call system 62. For example, when a patient positioned onboard patient support apparatus 20 speaks into a microphone to talk to a remotely positioned nurse, the audio signals from his or her voice are communicated via link 86 to specific pins of outlet 78 that are in communication with nurse call system 62 and that are different from the pins used for communications with television 72, room light 74, and reading light 76. Similarly, if patient support apparatus 20 detects that a patient has triggered an exit alert by exiting patient support apparatus 20, patient support apparatus 20 is configured to send an alert signal to nurse call system 62 via one or more pins of outlet 78 that are different from the pin(s) used to communicate the aforementioned audio signals, and that are also different from the pins used to communicate with television 72, room light 74, and reading light 76.

Room devices 72, 74, 76 are conventional room devices that are typically present in a conventional hospital room. In most cases, the particular brand and model of the television 72 and/or lights 74, 76 will vary from healthcare facility to healthcare facility, and may vary from room to room within the same healthcare facility. The different models and/or brands of televisions 72, room lights 74, and/or reading lights 76 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 72 and/or lights 74, 76 may vary from brand to brand and/or from model to model. Thus, in order for a patient to properly control the television 72 and/or lights 74, 76 using one of the patient control panels 54c, patient support apparatus 20 and/or headwall unit 70 need to be properly configured to match the particular television 72 and/or lights 74, 76 that are positioned in the same room as the patient support apparatus 20.

As shown in FIG. 4, patient support apparatus 20 is further configured to communicate with local area network 66 of the healthcare facility 56. In the example shown in FIG. 4, patient support apparatus 20 includes a network transceiver 90 (FIG. 5A) 126 that communicates wirelessly with local area network 66. It will be understood, however, that in some aspects, patient support apparatus 20 is adapted to communicate with network 66 via a wired connection, such as an Ethernet cable that plugs into an Ethernet port (e.g. an RJ-45 style port, an 8P8C port, etc.) built into patient support apparatus 20. Thus, network transceiver 90 may be an Ethernet transceiver in some aspects, or in other aspects it may be a wireless network transceiver, such as, but not limited to, a WiFi transceiver (e.g. IEEE 802.11) that wirelessly communicates with one or more wireless access points 68 of local area network 66. In still other aspects, patient support apparatus 20 includes both a wired port for communicating with network 66 via a wired connection and a wireless connection for communicating with network 66.

Patient support apparatus 20 may also be configured to communicate with one or more servers on local area network 66 of healthcare facility 56. One such server is a patient support apparatus server 82. Patient support apparatus server 82 is adapted, in at least one aspect, to receive status information from patient support apparatuses 20 positioned within healthcare facility 56 and distribute this status information to caregivers, other servers, and/or other software applications. In some aspects, patient support apparatus server 82 is configured to communicate at least some of the status data received from patient support apparatuses 20 to a remote server 88 that is positioned geographically remotely from healthcare facility 56. Such communication may take place via a network appliance 92, such as, but not limited to, a conventional router and/or a gateway, that is coupled to the Internet 94. The remote server 88, in turn, is also coupled to the Internet 94, and patient support apparatus server 82 is provided with the URL and/or other information necessary to communicate with remote server 88 via the Internet connection between network 66 and server 88.

It will be understood that the architecture and content of local area network 66 will vary from healthcare facility to healthcare facility, and that the example shown in FIG. 4 is merely one example of the type of network a healthcare facility may be employ. Typically, additional servers 96 will be hosted on network 66 and one or more of them may be adapted to communicate with patient support apparatus server 82. For example, an electronic health record server will typically be present in any healthcare facility, and in some cases may be in communication with patient support apparatus server 82 in order to receive patient data that is to be recorded in a patient's health record (e.g. weight readings taken from the scales built into patient support apparatuses 20; therapies provided to patients using powered mattresses 42 onboard patient support apparatuses 20, etc.). Local area network 66 will also typically allow one or more electronic devices 98 to access the local area network 66 via wireless access points 68. Such electronic devices 98 include, but are not limited to, smart phones, tablet computers, portable laptops, desktop computers, and other types of electronic devices that include a WiFi capability and that are provided with the proper credentials (e.g. SSID, password, etc.) to access network 66.

In at least one aspect, patient support apparatus server 82 is configured to communicate with one or more electronic devices 98 in order to allow such devices 98 to control one or more of the room devices 72, 74, 76 using one or more patient support apparatuses 20 as communication intermediaries. Thus, for example, if a user of an electronic device 98 wishes to turn off a television 72 positioned with a particular room, he or she can access patient support apparatus server 82 using electronic device 98 and its connection to local area network 66 via wireless access point 68. Patient support apparatus sever 82 executes an application that presents an authorized user of electronic device 98 with a set of menu options for controlling room devices 72, 74, 76 in at least one room 58, if not many or all, of the rooms 58 contained within healthcare facility 56. The user of electronic device 98 can then select the desired menu option on the screen of their electronic device 98 to turn on a room or reading light 74, 76, turn off a room or reading light 74, 76, turn on/off television 72, change the channel and/or volume of television 72, and/or change another aspect of television 72 (e.g. turn on/off closed captioning). The menu includes a selection of not only which rooms within healthcare facility 56 that electronic device 98 can be used for controlling room devices 72, 74, 76, but also which bays within any semi-private rooms that electronic device 98 is able to control the corresponding room devices 72, 74, 76.

FIG. 5 depicts in more detail various portions of, but not necessarily a complete, control system 100 onboard patient support apparatus 20. Control system 100 includes a pendant/siderail node 102a, a main node 102b, and a headwall communication node 102c. Each of nodes 102a-c are part of an onboard embedded communications network 106. That is, each node 102a-c is communicatively coupled to each other via an onboard communication network 106, which, in the illustrated aspect, is a Controller Area Network (CAN). It will be understood that other types of communication may be used in other aspects (e.g. one or more of the following: an I-Squared-C bus, a Local Interconnect Network (LIN) bus, Firewire, RS-232, RS-485, a Universal Serial Bus (USB), Ethernet, and/or a Serial Peripheral Interface (SPI) bus, as well as non-bus communication). In still other aspects, control system 100 may be implemented with fewer or greater numbers of nodes (including only a single node). Still other modifications are possible for control system 100, including, but not limited to, the elimination and/or replacement of onboard network 106.

Pendant/siderail node 102a includes pendant/siderail controller 108; main node 102b includes a main controller 110, and headwall communications node 102c includes a headwall communications controller 112. Each of controllers 108, 110, and 112 may take on a variety of different forms. In the illustrated aspect, each of controllers 108, 110, and 112 is implemented as a conventional microcontroller. However, controllers 108, 110, and 112 may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 108, 110, and 112 when carrying out the functions described herein, as well as the data necessary for carrying out these functions, are stored in a corresponding memory (not shown) that is accessible to that particular controller 108, 110, and 112.

In some aspects of patient support apparatus 20, siderail/pendant node 102a is physically positioned inside one or both of the head end siderails 36 of patient support apparatus 20 and includes patient control panel 54c. In other aspects, pendant/siderail node 102a is physically positioned inside of a pendant that is coupled, typically via a cable, to patient support apparatus 20. In still other aspects, patient support apparatus 20 may be configured with one or more pendant/siderail nodes 102a positioned inside of siderails 36 and also a pendant controller that is plugged into a pendant port on patient support apparatus 20 (and in communication with embedded network 106).

Control panel 54c of pendant/siderail node 102a includes a plurality of controls 50. Although FIG. 5 only illustrates controls 50g and 501 through 50r, it will be understood that pendant/siderail node 102a may include any or all of the controls 50 shown in FIG. 3. Pendant/siderail node 102a may also include additional controls 50 beyond what is shown in FIGS. 3 and/or 5, and/or it may include a selection of controls 50 that is different from the sets of controls 50 shown in FIGS. 3 and/or 5.

As shown in FIG. 5, pendant/siderail node 102a includes a nurse answer light 114 and a nurse call light 136. Pendant/siderail controller 108 is configured to light up nurse call light 136 when the user presses nurse call control 50g and receives an acknowledgement from the nurse call system 62 that a nurse call request has been successfully communicated to the nurse call system. Controller 108 is configured to light up nurse answer light 114 when a nurse actually responds to the nurse call placed by the user pressing on nurse call control 50g. These signals are passed back and forth between patient support apparatus 20 and the nurse call system via conductors 80, communications outlet 78, cable 84, headwall unit 70, and link 86. Headwall communication node 102c directly oversees and controls the wireless signals that are communicated between headwall unit 70 and patient support apparatus 20. That is, node 102c controls the communications over link 86.

Pendant/siderail node 102a includes a microphone/speaker 104 that is used by the patient when communicating with a remotely positioned nurse. The speaker 104 emits sound signals corresponding to the nurse's voice when the nurse is speaking, and the microphone 104 converts the sound signals of the patient's voice to electrical signals when the patient is speaking.

Control system 100 also includes a wireless network transceiver 90 adapted to wirelessly communicate with one or more of the wireless access points 68 of the local area network 66 of the healthcare facility 56. As was noted, in some aspects, transceiver 90 may be a conventional WiFi transceiver, although other types of wireless transceivers may be used. As was also noted previously, patient support apparatus 20 may also, or alternatively, include a wired transceiver (not shown) for communicating with network 66 via a wired connection.

Headwall communications node 102c includes an infrared transceiver 116 and a Bluetooth transceiver 118. Transceivers 116 and 118 are adapted to wirelessly communicate with headwall unit 70, and headwall communications node 102c controls the operation of transceivers 116 and 118. In some aspects, the signals that are sent from patient support apparatus 20 to headwall unit 70 are sent over both transceiver 116 and 118 in order to provide redundancy to these communications. In other aspects, these signals are sent over only one of the transceivers 116, 118, while in still other aspects, some data is sent via both transceivers 116, 118, while other data is only sent via one of these two transceivers 116, 118.

Headwall node controller 112 is adapted to forward commands received from any of controls 50 to headwall unit 70. Thus, for example, if a patient activates control 50q to shut off television 72, pendant/siderail controller 108 receives this command and forwards it to headwall node controller 112 (either directly, or via main node 102b). Headwall node controller 112, in turn, sends a signal to headwall unit 70 indicating that the television 72 is to be turned off. As noted, the signal may be sent via transceiver 116 or transceiver 118, or via both. As will be discussed in greater detail below, headwall unit 70 receives this signal and then adjusts the electrical characteristic of pin 34 (e.g. applies a sequence of voltages) of its headwall interface 132 in such a way so as to cause television 72 to be turned off.

Figure 5A:
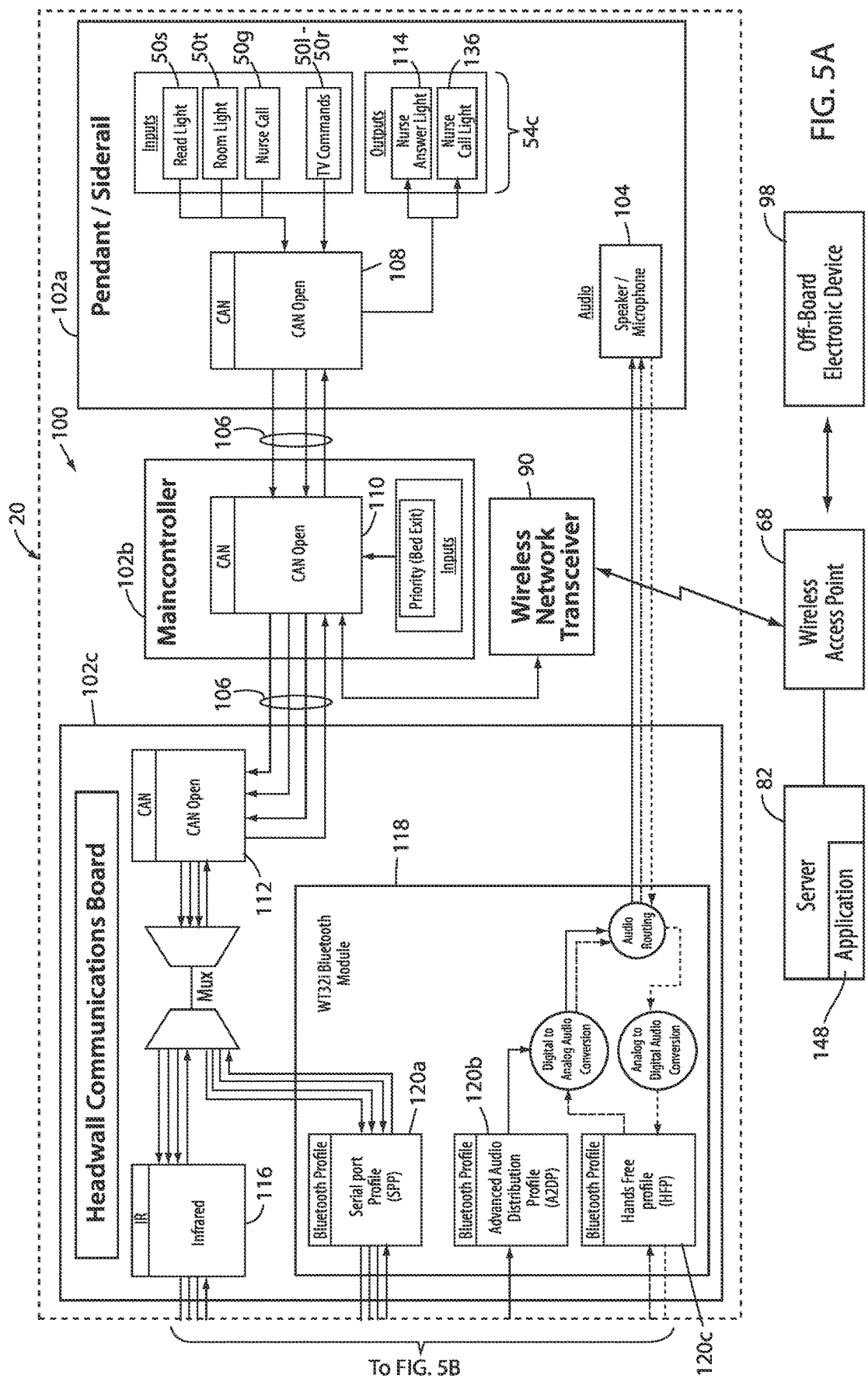
FIG. 5A is a first portion of a control system of the patient support apparatus.

As shown in FIG. 5A, Bluetooth transceiver 118 of headwall communications node 102*c* may utilize a plurality of different Bluetooth profiles 120-*c* when communicating with headwall unit 70. These include a serial port profile 120, an advanced audio distribution profile 120*b*, and a hand free profile 120*c*. In the illustrated aspect, Bluetooth transceiver 118 uses the serial port profile for communicating the commands to room devices 72, 74, and 76. Bluetooth transceiver 118 uses the other profiles 120*b* and 174*c* for transmitting the voice signals between patient support apparatus 20 and communications outlet 78 that arise when the patient onboard patient support apparatus 20 is talking to a remotely positioned nurse via nurse call system 62. The patient's voice signals are detected onboard patient support apparatus 20 via microphone 114 and sent to headwall unit 70 using transceiver 118. The nurse's voice signals are received from headwall unit 70 and forwarded to speaker 114. In some aspects, the speaker and microphone are the same device, such as shown by microphone/speaker 114 in FIG. 5A, while in other aspects, the speaker and microphone may be separate devices. Further, in some aspects, the management of Bluetooth transceiver 118 in communicating audio signals between headwall unit 70 and the speaker, microphone, and/or speaker/microphone is carried out in any of the manners disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

Headwall unit 70 (FIG. 5B) includes an infrared transceiver 122, a Bluetooth transceiver 124, a headwall unit controller 126, configuration circuitry 128, a television controller 130, and a headwall interface 132. Infrared transceiver 122 is adapted to communicate with infrared transceiver 116 of patient support apparatus 20 using infrared waves. Bluetooth transceiver 124 is adapted to communicate with Bluetooth transceiver 118 of patient support apparatus 20 using RF waves in accordance with the conventional Bluetooth standard (e.g. IEEE 802.14.1 and/or the standard maintained by the Bluetooth Special Interest Group (SIG) of Kirkland, Washington, USA). Headwall unit controller 126 is adapted to control the operation of transceivers 122, 124, configuration circuitry 128, TV controller 130, and headwall interface 132. Headwall unit controller 126 may be implemented as one or more microcontrollers, and/or in any of the same manners as controllers 108, 110, and/or 112, as discussed previously.

Headwall interface 132 (FIG. 5B) is an interface into which a conventional 37-pin nurse call cable, such as nurse call cable 84, is adapted to plug. That is, interface 132 is adapted to receive a 37-pin connector coupled to one end of a conventional nurse call cable 84. Headwall interface 132 includes a plurality of pins 134 (e.g. 37 pins) that are adapted to electrically communicate with corresponding pins on nurse call cable 84. In some aspects, pins 134 of headwall interface 132 may comprise female receptacles adapted to electrically couple to pins of cable 84 when cable 84 includes a male connector, or they may be pins 134 adapted to electrically couple to female receptacles when cable 84 includes a female connector. Pins 134 may alternatively be implemented as any type of metal, or electrically conductive, contact for establishing electrical communication between patient support apparatus 20 and nurse call cable 84.

Each pin 134 of headwall interface is adapted to convey certain information from patient support apparatus 20 to nurse call system 62 and/or room devices 72, 74, 76, or vice versa. FIG. 7 shows one illustrative pin assignment for a conventional 37-pin connector. As can be seen in FIG. 7, each pin conveys different information. For example, pin 3 is used to convey information to room light 74 indicating that the occupant of patient support apparatus 20 has pressed a control (e.g. 50*t*) on patient support apparatus 20 to turn on or turn off the room light 74 in the particular room in which patient support apparatus 20 is located. In many instances, pin 3 is electrically tied to pin 27 and patient support apparatus 20 sends commands to room light 74 to turn on or turn off based on whether the electrical connection between pins 3 and 27 is open or closed. For some room lights 74, an open circuit between pins 3 and 27 indicates that the room lights should be turned off and a closed circuit between pins 3 and 27 indicates that the room light 74 should be turned on. For other room controls, the opposite may be true. That is, for some other room lights 74, an open circuit between pins 3 and 27 indicates the room light 74 should be turned on and a closed circuit between pins 3 and 27 indicates the room light 74 should be turned off.

As another example, pin 2 (FIG. 7) is commonly used to control a reading light 76. When the occupant of patient support apparatus 20 presses a control (e.g. 50*s*) on control panel 54*c* of patient support apparatus 20, controller 108 sends a message to headwall controller 112, which responds by forwarding one or more signals to headwall unit 70 via BT transceiver 118 and/or IR transceiver 116. Those signals are detected by IR transceiver 122 and/or BT transceiver 124 and forwarded to headwall unit controller 126, which then sends the appropriate signals to headwall interface 132 that cause headwall interface 132 change a voltage and/or an open or closed state between pins 2 and 27 of headwall interface 132. For some reading lights 76, an open circuit between pins 2 and 27 indicates that the reading light 76 should be turned off and a closed circuit between pins 2 and 27 indicates that the reading light 76 should be turned on. For other reading lights 76, the opposite may be true.

When an occupant of patient support apparatus 20 presses on any of television controls 50*l-r* on control panel 54*c*, pendant/siderail controller 108 sends a corresponding message over communication network 106 to headwall controller 112 of headwall communications node 102*c* (FIG. 5A). Headwall controller 112 responds by forwarding one or more signals to headwall unit 70 via BT transceiver 118 and/or IR transceiver 116. Those signals are detected by IR transceiver 122 and/or BT transceiver 124 and forwarded to headwall unit controller 126. In response, headwall controller 126 controls headwall interface 132 such that it outputs a corresponding signal on pins 33 and 34 of headwall interface 132. Because these pins are electrically coupled to the television 72 within room 58 via nurse call cable 84, communications outlet 78, and conductors 80, the television reacts appropriately in response to the commands entered by the occupant using controls 50*l-r*.

Figure 5B:
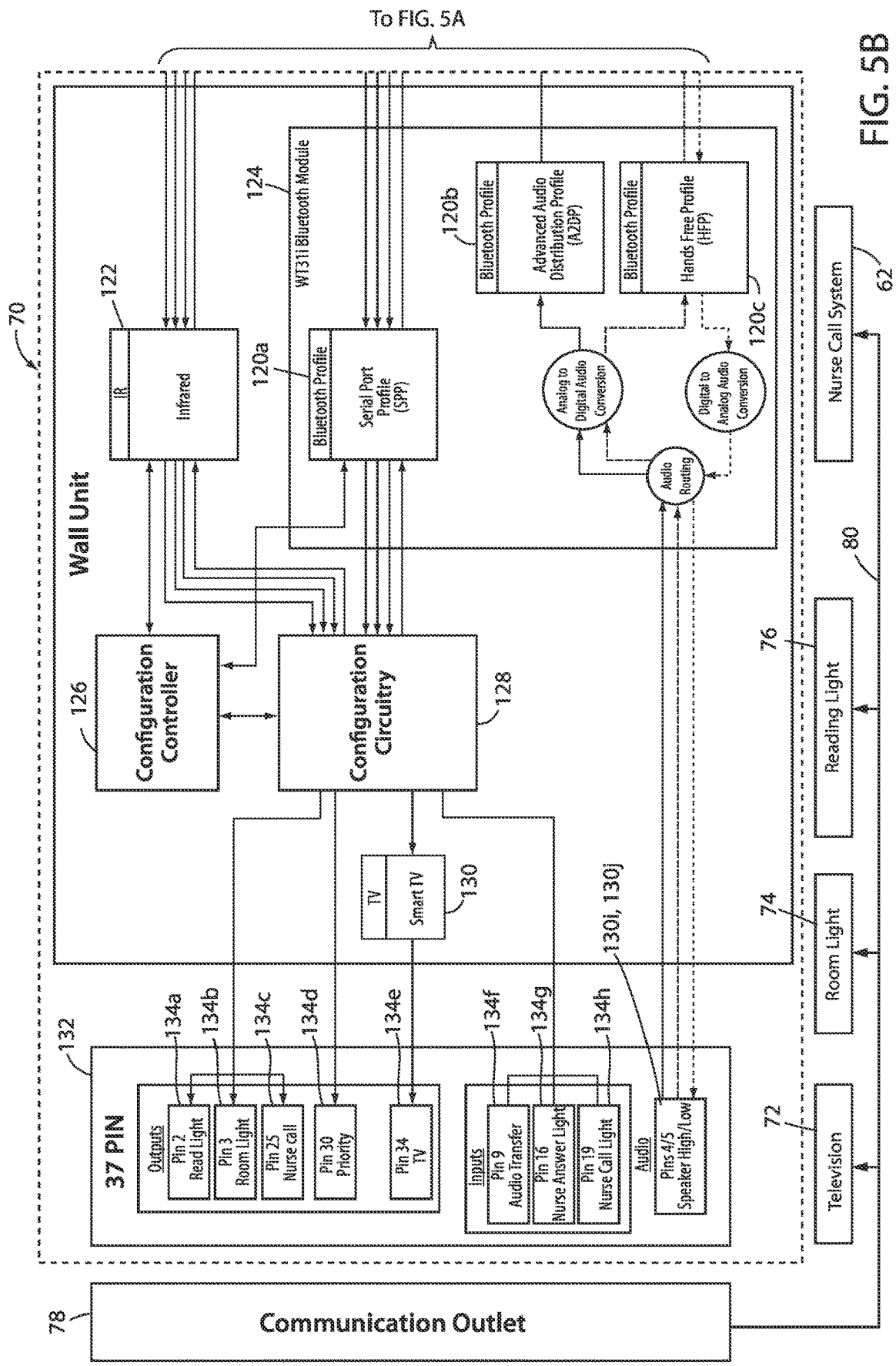
FIG. 5B is a second portion of the control system of the patient support apparatus.

In order for headwall controller 126 to determine how to properly respond to the messages it receives from patient support apparatus 20 in response to a user pressing on one or more of the controls 50 used to control television 72, room light 74, and/or reading light 76, controller 126 utilizes configuration circuitry 128 (FIG. 5B). Configuration circuitry 128 is set up to maintain the pins 134 in their appropriate neutral state until a user presses on a corresponding control 50, as well as to apply the proper voltage to each of pins 134 in response to the user pressing the corresponding control 50. In some aspects, configuration circuitry 128 includes one or more dip switches, or other devices, that are configurable to match the room device 72, 74, 76, and nurse call system 62 of the healthcare facility 56 in which the patient support apparatus 20 is installed. In other aspects, configuration circuitry 128 may include onboard non-volatile memory that stores the necessary configuration data, along with appropriate circuitry to utilize this stored data to implement the necessary state changes in pins 134. In at least one aspect, configuration circuitry 128 is implemented in any of the manners disclosed in commonly assigned U.S. patent publication 2018/0293849 published on Oct. 11, 2018, entitled PATIENT SUPPORT APPARATUSES WITH RECONFIGURABLE COMMUNICATION, the complete disclosure of which is incorporated herein by reference. Still other manners of implementing configuration circuitry 128 may also or alternatively be implemented according to the present disclosure.

Television controller 130 (FIG. 5B) stores the sequence and voltage levels of signals that are to be sent for various brands of televisions that are necessary to control that television's channel, volume, mute, closed captioning, power state, HDMI input, etc. In such cases, either headwall controller 126 and/or configuration circuitry 128 informs TV controller 130 which brand of television (and, in some cases, which model) is in room 60, and TV controller 130 thereafter determines the correct signals to send in response to television control commands received from patient support apparatus 20 (that are, in turn sent in response to a user pressing on one or more of the television controls 50l-r). As will be discussed in more detail below, the knowledge of which brand of television 72 is present in the room is automatically determined by controller 126 in response to IR signals that are emitted by a conventional television remote control used for that particular television and detected by IR transceiver 122. That is, IR transceiver 122, in addition to detecting IR signals conveyed from the IR transceiver 116 onboard patient support apparatus 20, is also configured to detect conventional IR signals emitted from conventional television remote controls, and to determine which brand and/or type of television emitted those remote control signals. This brand/type information is then forwarded to television controller 130 which includes a table, or some other data structure, that matches the correct signals to use for each brand/type of television. That is, when television controller 130 is informed of a specific brand/type of television, it is able to consult its memory to determine what the proper command set is for controlling that particular television. In some aspects, television controller 130 is a commercially available conventional television controller, such as one marketed by Curbell Medical of Orchard Park, New York.

In addition to room devices 72, 74, 76, the various pins 134 of headwall interface 132 also communicate information to nurse call system 62. This information is likewise often communicated by opening or closing the electrical connection between two pins. For example, when a patient presses a nurse call control, such as nurse call control 50g (FIG. 3), the electrical connection between pins 19 and 28 is typically changed by headwall controller 126 and configuration circuitry 128. These pins indicate to the nurse call system 62 that a nurse call request has been initiated by the occupant of patient support apparatus 20. Depending upon the particular nurse call system 62, it responds by illuminating one or more lights (e.g. a light in the hallway of the healthcare facility and/or a light at one or more of the nurses' stations 64). For some nurse call systems, the neutral state of the electrical connection between pins 19 and 28 should be open, while in other nurse call systems, the neutral state should be closed. Accordingly, configuration circuitry 128 is configured to properly match the particular nurse call system 62 with which it is going to communicate.

The term "neutral state" used herein refers to the state of the electrical connection between two pins 134 when no condition has been detected, or no desired action has been requested by the patient, caregiver, or patient support apparatus 20 itself. Thus, for example, for the pin that communicates a nurse call signal to the nurse call system (e.g. pin 30), the neutral state of that pin refers to its state when no nurse call control (e.g. 50g) has been pressed. In some nurse call systems, this neutral state will be closed with respect to a ground pin (e.g. common pin 31), while for other nurse call systems, this neutral state may be open with respect to the ground (e.g. common pin 31). As another example, for the pin that communicates a change to room light 74, the neutral state of pin 3 may refer to the electrical state of pin 3 relative to pin 27 (e.g. open or closed) when no change in room light 72 is being requested by a user (e.g. the patient has not pressed, or otherwise activated, control 50t).

When headwall unit 70 receives a command to change a feature of one of the room devices 72, 74, and/or 76 from one, or both, of transceivers 122, 124, headwall controller 126 interprets the command so as to control configuration circuitry 128 in a manner that leads to the correct electrical change on the correct pins 134 of headwall interface 132. For example, if headwall unit 70 receives a command from patient support apparatus 20 for turning off reading light 76, headwall unit controller 126 controls configuration circuitry 128 such that the electrical state of pin 2 (a.k.a. pin 134a) is changed. As noted previously, this change in state may vary, depending upon the model and/or implementation of the reading light 76. In some aspects, headwall interface 132 may open the connection between pin 2 and pin 27 to turn off reading light 76; in other aspects, it may close this connection; while in still other aspects, it may change the voltage on pin 2 and/or perform some other electrical change.

Similarly, headwall controller 126 and configuration circuitry 128 are configured to change the electrical characteristic of pin 3 (a.k.a. pin 134b) when a command is received from patient support apparatus 20 to change a status of room light 74. Headwall unit controller 126 and configuration circuitry 128 are also configured to change the electrical characteristic of pin 25 (a.k.a. pin 134c) when a patient onboard patient support apparatus 20 places a call to a remotely positioned nurse (e.g. presses no nurse call control 50g). Still further, headwall unit controller 126 and configuration circuitry 128 are also configured to perform the following: (a) change the electrical characteristic of pin 30 (a.k.a. pin 134d) when an exit detection system onboard patient support apparatus 20 detects a patient exit; (b) change the electrical characteristic of pin 34 (a.k.a. pin 134) when a command is received from patient support apparatus 20 to change a feature of television 72; (c) change the electrical characteristic of pin 9 (a.k.a. pin 134f) when the patient is speaking and patient support apparatus 20 is attempting to send audio signals to the remote nurse via headwall unit 70; (d) read the current electrical state of pin 16 (a.k.a. pin 134g) to determine when a remotely positioned nurse has answered a patient call and to then send a command to patient support apparatus 20 to illuminate nurse answer light 114; (e) read the current electrical state of pin 19 (a.k.a. pin 134*h*) to determine when a remotely positioned nurse has placed a call to the patient and to send a command to patient support apparatus 20 and to illuminate nurse call light 136; and (f) transfer audio signals between patient support apparatus 20 and nurse call system 62 using pins 4 and 5 (a.k.a. pins 134*i* and 130*j*).

Headwall unit 70 includes an electrical cord 138 (FIG. 4) that is adapted to be inserted into a conventional electrical outlet 140. Electrical cord 138 enable headwall unit 70 to receive power from the mains electrical supply via outlet 140. It will be appreciated that, in some aspects, headwall unit 70 is battery operated and cord 138 may be omitted. In still other aspects, headwall unit 70 may be both battery operated and include cord 138 so that in the event of a power failure, battery power supplies power to headwall unit 70, and/or in the event of a battery failure, electrical power is received through outlet 140.

Headwall unit 70, as noted, controls the wireless communication between patient support apparatus 20 and communications outlet 78. In addition to communicating the signals used to control room devices 72, 74, and/or 76, headwall unit 70 may also communicate the following information between patient support apparatus 20 and communications outlet 78: messages indicating the current status of one or more siderails 36 of patient support apparatus 20 (e.g. whether the side rails are up or down, or have changed position); messages indicating the current status of a brake on patient support apparatus 20; messages indicating the current status of the height of support deck 30 relative to base 22 (e.g. such as whether support deck 30 is at its lowest height or not); messages indicating the current angle of head section 44; messages indicating the current status of an exit detection system (e.g. whether the exit detection system is armed or not); messages indicating the current charging status of one or more batteries on patient support apparatus 20; messages indicating the current status of an alternating current (A/C) power cable on patient support apparatus 20 (e.g. whether it is plugged in or not); diagnostic information about patient support apparatus 20; messages containing patient data gathered from one or more sensors on board patient support apparatus 20; message containing patient data gathered from one or more medical devices that are separate from patient support apparatus 20 but which communicate such data to patient support apparatus 20; and/or any other messages containing information about patient support apparatus 20, the patient supported thereon, and/or a caregiver associated with the patient.

In addition to communicating the aforementioned data between patient support apparatus 20 and communications outlet 78, headwall unit 70 may also communicate location data to patient support apparatus 20 that enables patient support apparatus 20 and/or patient support apparatus server 82 to determine the location of patient support apparatus 20 within healthcare facility 56. Such location determination may be carried out in any of the manners disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall unit 70 may also perform additional functions. In some aspects, headwall unit 70 may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some aspects, headwall unit 70 may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other aspects, headwall unit 70 may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference. Still further, in some aspects, headwall unit 70 may also, or alternatively, perform any of the same functions performed by the headwall units 68 disclosed in commonly assigned U.S. patent application Ser. No. 63/193,777 filed May 27, 2021, by inventors Thomas Deeds et al. and entitled SYSTEM FOR ASSOCIATING MEDICAL DATA, the complete disclosure of which is incorporated herein by reference.

When a user presses on, or otherwise activates, any of controls 50 on control panel 54*c*, the pressing of those controls is detected by pendant/siderail controller 108 (FIG. 5A). In response thereto, controller 108 sends a message on network 106 to headwall communication node 102*c* indicating which control(s) 50 were pressed. In some aspects, the message is addressed (or otherwise identified) as being intended for headwall communication node 102*c* so that main node 102*b* does not need to act as a communications intermediary between node 102*a* and node 102*c*. In other aspects, controller 108 may send the message to node 102*c* via one or more intermediary nodes, such as main node 102*b*. However the message travels to node 102*c*, headwall communication controller 112 is programmed to receive the message and convey it in the appropriate manner to headwall unit 70 via infrared transceiver 116 and/or via Bluetooth transceiver 118.

As was discussed previously, if the message is a television command, headwall unit controller 126 needs to inform television controller 130 of the type/brand of television that is positioned within the room 58 in order for television controller 130 to send the correct signals to television 72 to carry out the desired command. In other words, different brands of televisions often require different voltage levels and/or different sequences of voltages in order to carry out the same command (e.g. increase a channel). In prior art patient support apparatuses, the patient support apparatuses and/or headwall units were manually informed by a technician of what brand of television 72 was positioned within the room during a configuration process. In the patient support apparatuses 20 and/or headwall units 70 of the present disclosure, the brand of television is automatically determined based on infrared signals emitted from a conventional television remote control, thereby relieving the caregiver and/or technician of the requirement of performing a manual configuration process for patient support apparatus 20 and/or headwall unit 70.

In one aspect, headwall unit 70 is adapted to automatically determine the type/brand of television 72 that is positioned within a room 58 by analyzing the signals that are emitted when a person presses on a conventional television remote control. FIG. 4 illustrates a conventional television remote control 150 that is adapted to control television 72. Remote control 150 is often sold with television 72 when the healthcare facility 56 purchases television 72. However, remote control 150 may be an after-market product. However purchased, remote control 150 is configured to control the particular type and/or brand of television 72 that is positioned within room 58. Remote control 150 includes a plurality of buttons, or other controls, that, when pressed, enable the user to control television 72 without having to press on any buttons, or other controls that are physically integrated into television 72.

When a user presses on a button on remote control 150, such as, for example, a button to increase the volume of the audio of television 72, remote control 150 emits an infrared signal that is sent to television 72 and that instructs television 72 to increase its volume. Remote control 150 therefore communicates with television 72 directly via infrared signals. Such infrared communication is conventional for television remote controls, and each infrared packet of information that is sent by remote control 150 to television 72 includes a header that contains a unique code 152 (FIGS. 6A-6G) that corresponds to the particular brand/type of television that remote control 150 is configured to control. A list of these codes 152 is shown in FIGS. 6A-6G, as well as the corresponding brand of television 154 (in bold) for each of these codes.

Controller 126, or a memory that controller 126 has access to, stores the list of codes shown in FIGS. 6A-6G. Whenever infrared transceiver 122 onboard headwall unit 70 detects an infrared signal, controller 126 analyzes it to determine if it is a signal from patient support apparatus 20 (i.e. infrared transceiver 116) or if it is a signal from remote control 150. Controller 126 performs this analysis based on the known characteristics of the signals from patient support apparatus 20 and the known characteristics of the signals from conventional television remote controls 150. In some aspects, each signal from patient support apparatus 20 includes a unique identifier and/or a signature format, data segment, and/or other information that allows controller 126 to identify that those signals came from a patient support apparatus 20 (rather than another source). For those signals that are emitted by remote control 150, controller 126 analyzes these to decipher the code 152 that is embedded within these signals, and once the code is determined, to use the data, such as that shown in FIGS. 6A-6G, that is has stored in memory to determine the brand of television 72. Controller 126 then forwards this identification to television controller 130, which in turns uses it to determine the proper command set to use in the future when sending commands to the television control pin 134 (e.g. pin 34) of communication outlet 78 so that television 72 will respond correctly when a user presses on any of the television controls 50*l-r*.

After controller 126 has determined which television brand the remote control 150 is designed to control, controller 126 stores this information in a memory onboard wall unit 70 and continues to use it for all future television command signals that it receives from patient support apparatus 20. Thus, a user needs to only press on one button of the television remote control 150 while in the vicinity of headwall unit 70, and controller 126 (along with IR transceiver 122) is configured to determine the type/brand of television that the remote control 150 is intended to control, to save that information, and to use that information in the future whenever a patient activates any of television controls 50*l-r*. After pressing that single button (although more than one button may be pressed, if desired), remote control 150 need not be used anymore (if desired), and the patient can instead use control panel 54*c* for any future television commands.

It should be noted that regardless of which button a user presses on the conventional remote control 150, such conventional remote controls are configured to emit the same code 152 for all of the television commands. Thus, it is unnecessary for the user of the remote control 150 to select a specific command (e.g. channel change, power on/off, etc.) when using the remote control 150. Instead, IR transceiver 122 will detect whatever command is sent from remote control 150, and that command will include the code 152, which controller 126 will use to determine the corresponding television type/brand in the manner mentioned above.

However, in some embodiments, headwall unit 70 may be configured such that a user must press one or more buttons and/or sequences of buttons on the TV remote control 150 that are known to headwall unit 70. In other words, in some embodiments, headwall unit 70 is configured to look for IR signals from television remote control 150 that correspond to a particular button, or sequence of buttons (e.g. volume up, channel up, closed captioning) that is stored in a memory onboard headwall unit 70. Headwall unit 70 may then correlate the specific IR signals emitted from the television remote control for that particular button, or sequence of buttons, to a specific brand and/or model of television.

In some aspects, headwall unit 70 is configured such that whenever it is powered, controller 126 automatically analyzes all IR communications that are detected by IR transceiver 122 to determine if they are television remote control signals (from remote control 150). In such aspects, controller 126 is further configured to automatically store the television code 152 (or corresponding TV brand/type) in memory whenever it detects a television remote control signal, as well as inform TV controller 130 of the television brand/type. It is therefore not necessary for the user of remote control 150 to press any buttons on headwall unit 70 or on patient support apparatus 20, or take any other actions with respect to headwall unit 70 or patient support apparatus 20, when he or she wishes to "inform" headwall unit 70 of the type of television 72 that is positioned within the room. All that is required is that the user position the remote control at a location in which its infrared signals will be detected by IR transceiver 122, and then press a control on television remote control 150. In some aspects, IR transceiver 122 is positioned to detect infrared signals from the remote control 150 at most locations within room 58.

In some aspects, headwall unit 70 provides feedback to a user regarding the automatic detection process of the type/brand of television 72, such as, but not limited to, the television type/brand that was currently detected (or not detected), the television brand/type that headwall unit 70 was previously configured to control (if any), and/or the fact that a new type of television remote control signal has been detected. In some aspects, controller 126 forwards any or all of this information to patient support apparatus 20 using one or both of transceivers 122, 124, and patient support apparatus 20 is configured to display all or some of this information on one or more of its onboard displays (e.g. display 52). In other aspects, headwall unit 70 may include its own display and/or lights that controller 126 controls in order to convey this information directly to the user (i.e. without sending it to patient support apparatus 20). In still other aspects, controller 126 may be configured to both display such feedback information locally and remotely (e.g. on patient support apparatus 20). In some aspects, patient support apparatus 20 is configured to forward the identified television brand/type to patient support apparatus server 82, which may further be configured to forward such information to one or software applications 148 (FIG. 5A). Such software applications may be in communication with one or more electronic devices 98.

In some aspects, if controller 126 detects a television control signal from remote control 150 for the first time, or detects a television control signal form a different remote control 150 (than one previously detected), it may be configured to notify the user that a new television type/brand has been detected, and to therefore request confirmation from the user that it should switch to using television commands that correspond to the new television type/brand. In such aspects, the notification to the user, as well as the request for confirmation, may be carried out by sending a message to patient support apparatus 20, which then displays the notification and confirmation request, or controller 126 may provide the notification and request for confirmation directly via a display, lights, and/or other indicators that are built into headwall unit 70.

It will also be understood by those skilled in the art that patient support apparatus 20 may be configured to perform the automatic television identification process that headwall unit 70 has been described herein as carrying out. That is, in some aspects of patient support apparatus 20, controller 110 (or another one of the controllers onboard patient support apparatus 20) may be configured to analyze the infrared signals that are detected by IR transceiver 116 to determine if they are IR signals that have been emitted by headwall unit 70, or if they are IR signals that have been emitted by a remote control 150. If controller 110 determines that the signals were from a remote control 150, it determines the television type/brand that those signals correspond to in the same manner previously discussed with respect to controller 126 of headwall unit 70. After determining the television brand/type, controller 110 sends a message to headwall unit 70 informing it of the type of television 72 that is positioned within the room. Controller 126 receives this information and forwards it to television controller 130, which uses it in the aforementioned manner. Controller 110 may further be configured to display on display 52 any of the feedback notification and/or confirmation information mentioned above (e.g. notification of a new television remote control signal being detected; an identification of the new television brand/type; an identification of an old television brand/type; confirmation that a switch from a previous television type/brand is to be made; etc.).

In some aspects, headwall unit 70 are constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. In such aspects, each headwall unit 70 includes a unique identifier that corresponds to its particular location within the healthcare facility, and either patient support apparatus 20 or server 82 is configured to use this unique identifier to determine where patient support apparatus 20 is located. Such location information is determined from the fact that patient support apparatus 20 is only able to receive this unique identifier from a headwall unit 70 when the patient support apparatus 20 is positioned adjacent (e.g. with five to ten feet) of the headwall unit 70.

According to another alternative aspect of the present disclosure, controller 126 of headwall unit 70 (or a controller onboard patient support apparatus 20) may be configured to analyze other information within the IR signals emitted from television remote 150 in lieu of, or in addition to, the television codes 152. That is, in some aspects, controller 110 (or a controller onboard patient support apparatus 20) compares a data stream of signals emitted from remote control 150 (and detected by the IR transceiver 122 or 116) to known data streams for particular models of televisions (which are stored in a memory accessible to the controller) and uses this comparison process to automatically determine the model of the television 72. In such cases, the user may be instructed to activate one or more specific commands using television remote control 150, where such specific commands are known to the controller 110, or controller 110 is informed of the specific commands. In such cases, controller 110 checks an accessible database of known data streams for those particular commands for various television models, and is thereby able to discern what television brand/model is in the room 58.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described aspects. This disclosure is presented for illustrative purposes and should not be interpreted as an exhaustive description of all aspects or to limit the scope of the claims to the specific elements illustrated or described in connection with these aspects. For example, and without limitation, any individual element(s) of the described aspects may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A headwall unit adapted to be mounted to a headwall of a room in a healthcare facility, the headwall unit comprising:

an outlet interface adapted to electrically couple to a wall outlet mounted in the headwall, the outlet interface including a set of pins adapted to electrically couple to a plurality of conductors defined in the wall outlet when the outlet interface is coupled to the wall outlet, and the set of pins including a television control pin adapted to electrically couple to a television control conductor defined in the wall outlet;

a first infrared transceiver adapted to wirelessly communicate with a second infrared transceiver positioned onboard a patient support apparatus when the patient support apparatus is positioned adjacent to the headwall unit; and a controller adapted to analyze signals detected by the first infrared transceiver to determine if the signals were emitted by a television remote control, and, if so, to determine a type of television that the television remote control is adapted to control, and to forward a television control message to the television control pin in response to receipt of a television command from the patient support apparatus.

2. The headwall unit of claim 1 wherein the controller is further adapted to determine the type of television that the television remote control is adapted to control by analyzing a header within a packet sent by the television remote control.

3. The headwall unit of claim 1 further comprising a first RF transceiver adapted to wirelessly communicate with a second RF transceiver positioned onboard the patient support apparatus.

4. The headwall unit of claim 3 wherein the first RF transceiver is adapted to receive the television command from the patient support apparatus.

5. The headwall unit of claim 1 wherein the type of television includes a brand of the television.

6. The headwall unit of claim 1 wherein the controller is adapted to change the television control message based on the type of television and based on the television command received from the patient support apparatus.

7. The headwall unit of claim 6 wherein the television command is one of a channel changing command, a volume changing command, a closed-captioning command, or a power command.

8. The headwall unit of claim 1 wherein the first infrared transceiver is further adapted to transmit a unique identifier to the patient support apparatus, and wherein the unique identifier differentiates the headwall unit from other headwall units positioned within the healthcare facility.

9. The headwall unit of claim 3 wherein the controller is further adapted to receive an exit detection signal from the patient support apparatus via the first RF transceiver and to change a voltage on a particular pin of the set of pins in response to receipt of the exit detection signal.

10. A headwall unit adapted to be mounted to a headwall of a room in a healthcare facility, the headwall unit comprising:
an outlet interface adapted to electrically couple to a wall outlet mounted in the headwall, the outlet interface including a set of pins adapted to electrically couple to a plurality of conductors defined in the wall outlet when the outlet interface is coupled to the wall outlet, and the set of pins including a television control pin adapted to electrically couple to a television control conductor defined in the wall outlet;
a first RF transceiver adapted to wirelessly communicate with a second RF transceiver positioned onboard a patient support apparatus positioned adjacent to the headwall unit;
an infrared receiver adapted to receive signals from a television remote control; and
a controller adapted to determine a type of television the television remote control is adapted to control based on an analysis of the signals, to generate a television control message based on the type of television, and to forward the television control message to the television control pin in response to receipt of a television command from the patient support apparatus.

11. The headwall unit of claim 10 wherein the controller is further adapted to receive an exit detection signal from the patient support apparatus via the first RF transceiver and to change a voltage on a particular pin of the set of pins in response to receipt of the exit detection signal.

12. The headwall unit of claim 10 wherein the set of pins includes an audio pin and the controller is adapted to receive a plurality of audio signals from the television via the audio pin, and wherein the controller is further adapted to transmit the audio signals to the patient support apparatus via the first RF transceiver.

13. The headwall unit of claim 10 wherein the controller is further adapted to determine the type of television that the television remote control is adapted to control by analyzing a header within a packet sent by the television remote control.

14. The headwall unit of claim 10 wherein the first RF transceiver is adapted to receive the television command from the patient support apparatus.

15. The headwall unit of claim 10 wherein the type of television includes a brand of the television.

16. The headwall unit of claim 1 wherein the controller is adapted to change the television control message based on the television command received from the patient support apparatus.

17. The headwall unit of claim 16 wherein the television command is one of a channel changing command, a volume changing command, a closed-captioning command, or a power command.

18. The headwall unit of claim 10 wherein the infrared receiver is part of an infrared transceiver, and the infrared transceiver is adapted to transmit a unique identifier to the patient support apparatus, the unique identifier differentiating the headwall unit from other headwall units positioned within the healthcare facility.

* * * * *